(12) United States Patent
Yanagihara et al.

(10) Patent No.: US 7,667,063 B2
(45) Date of Patent: Feb. 23, 2010

(54) METHOD FOR PRODUCING TRIALKYL GALLIUM

(75) Inventors: Hisayoshi Yanagihara, Tokushima (JP); Atau Ioku, Tokushima (JP); Takatoshi Mori, Tokushima (JP); Hikari Mitsui, Tokushima (JP)

(73) Assignee: Nichia Corporation, Anan-Shi Tokushima (JP)

( * ) Notice: Subject to any disclaimer, the term of this patent is extended or adjusted under 35 U.S.C. 154(b) by 0 days.

(21) Appl. No.: 11/385,687

(22) Filed: Mar. 22, 2006

(65) Prior Publication Data

US 2006/0214161 A1     Sep. 28, 2006

(30) Foreign Application Priority Data

| Mar. 23, 2005 | (JP) | ............................. | 2005-085047 |
| Mar. 23, 2005 | (JP) | ............................. | 2005-085048 |
| Mar. 23, 2005 | (JP) | ............................. | 2005-085050 |
| Mar. 23, 2005 | (JP) | ............................. | 2005-085052 |
| Mar. 23, 2005 | (JP) | ............................. | 2005-085053 |

(51) Int. Cl.
*C07F 5/00* (2006.01)

(52) U.S. Cl. .............................. 556/1; 556/2

(58) Field of Classification Search .................... 556/1, 556/2; 257/40
See application file for complete search history.

(56) References Cited

U.S. PATENT DOCUMENTS

| 4,604,473 A | 8/1986 | Cole-Hamilton et al. |
| 4,904,616 A | * | 2/1990 | Bohling et al. ............... 117/104 |
| 5,248,800 A | 9/1993 | Smit et al. |

FOREIGN PATENT DOCUMENTS

| DE | 231568 | * | 2/1986 |
| GB | 2 123 423 A | | 2/1984 |
| JP | 1-301684 A | | 12/1989 |
| JP | 3-123784 A | | 5/1991 |
| JP | 3-127795 A | | 5/1991 |
| SU | 388563 B | | 6/1971 |
| SU | 325487 B | | 5/1974 |
| SU | 325847 B | | 5/1974 |

OTHER PUBLICATIONS

Bregadze et al., Journal of Cluster Science, vol. 13, No. 4, pp. 631-636, (Dec. 2002).
Starowieski et al., Applied Organometallic Chemistry, vol. 3, pp. 219-224, (1989).
Cymbaluk et al., Inorg. Chem., vol. 19, pp. 2381-2384, (1980).
Mains et al., Journal of Molecular Structure, vol. 274, pp. 277-287, (1992).
Akobiya et al., Journal of Organmetallic Chemistry, vol. 467, pp. 161-163, (1994).
Miehr et al., Organometallics, Vol. 15, No. 8, pp. 2053-2059, (1996).
Koide et al., Polyhedron, vol. 17, No. 5-6, pp. 983-991, (1998).
Gynane et al., Journal of Organometallic Chemistry, vol. 40, Chapter 6, No. 2, pp. C59-C60, (Jul. 16, 1972).
Jones et al., J. Chem. Soc. Dalton Trans. pp. 1047-1049, (1983).
Zakarkin et al., Russian Chemical Bulletin, vol. 46, No. 2, pp. 379-380, (Feb. 1997).
Eisch, J.J., Comprehensive Organometallic Chemistry, Ed. Wilkinson et al., vol. 1, pp. 157-251, (1982).
Kovar et al., Inorganic Chemistry, vol. 14, No. 11 pp. 2809-2813, (1975).
Kraus et al., Chemistry: Kraus and Toonder, Proc. Natl. Acad. Sci., vol. 19, pp. 292-298, (1933).
Coates, Coates: Trimethylgallium. Part I, J. Chem. Soc., No. 446, pp. 2003-2013, (1951).
Pearson et al., Study of the Entrainment Method, J. Org. Chem., vol. 24, pp. 504-509, (Apr. 1959).
Wilkinson et al., Journal of Organometallic Chemistry, vol. 93, pp. 39-42, (1975).
Lind et al., Journal of Organometallic Chemistry, vol. 36, pp. 35-39, (1972).
Lind et al., Journal of Organometallic Chemistry, vol. 40, pp. 35-41, (1972).
Lindsell et al., Comprehensive Organometallic Chemistry, Ed. Wilkinson et al., Chapter 4, vol. 1, pp. 156-252, (1982).
Gilman et al., Journal of Organmetallic Chemistry, vol. 2, pp. 447-454, (1964).
Jones, Chemtronics, vol. 4, pp. 15-25, (Mar. 1989).
Jones et al., Journal of Crystal Growth, vol. 68, pp. 1-9, (1984).
Bregadze et al., Organometallic Chemistry in the USSR, vol. 1, No. 3, pp. 281-290, (1988).
Yasuda et al., Organometallic Chemistry Reviews, vol. 2, pp. 255-277, (1967).
Zuckerman et al., Inorganic Reactions and Methods, vol. 10, pp. 170-177, (1989).
Suzuki et al., Journal of the Chemical Society of Japan, vol. 9, pp. 1414-1417, (1984).
Kabachnikov, Dolk. Akad. Nauk SSSR, vol. 212, pp. 880-881, (1973).
Gabrilenko et al., Izv. Akad. Nauk SSSR, Ser. Khim., vol. 126, pp. 126-127, (1972).
Gribov et al., Behavior of Trace Impurities During The Synthesis of Organometallic Compounds, Academy of Science of the USSR, vol. 208, No. 4, pp. 13-15, (Feb. 1973).

(Continued)

*Primary Examiner*—Shailendra Kumar
(74) *Attorney, Agent, or Firm*—Birch, Stewart, Kolasch & Birch, LLP

(57) ABSTRACT

The present invention provides method 1 for producing a trialkyl gallium comprising the steps of reacting gallium, magnesium, and an alkyl halide in an ether, and diluting during the reaction the reaction system with an ether; method 2 for producing a trialkyl gallium comprising the steps of heating in a vacuum a mixture of magnesium and molten gallium, and reacting the mixture with an alkyl halide in a solvent; and method 3 for producing a trialkyl gallium comprising the step of reacting an alkyl metal with an alkylgallium halide compound represented by the formula $$Ga_2R_mX_{6-m}$$

wherein R is a methyl or ethyl group, X is a halogen atom, and m is an integer from 1 to 5.

19 Claims, No Drawings

OTHER PUBLICATIONS

Bregadze et al., Institute of Heteroorganic Compounds, Academy of Sciences of the USSR, Moscow, Doklady Chemistry, vol. 212, No. 4, pp. 880-881, (Oct. 1973).

Database WPI, Section Ch, Week 197716, Derwent Publication Ltd., London, GB; AN 1977-2856OY and SU 388563.

Fukin et al., Transactions of Chemistry and Chemical Technologies, J13060013, No. 4, p. 40, (1973).

Database WPI, Section Ch, Week 197439, Derwent Publications Ltd., London, GB, AN 1974-69001V. (May 16, 1974) and SU 325847.

Akobiya et al., Journal of Organometallic Chemistry, vol. 467, pp, 161-163 (1994).

Zakharkin et al., Russian Chemical Bulletin, vol. 46, No. 2, pp. 379-380 (Feb. 1997).

Kovar at al., Inorganic Chemistry, vol, 14, No. 11 pp. 2809-2814 (1975).

Gilman et al., Journal of Organometallic Chemistry, vol, 2, pp. 447-454 (1964).

Bregadze at ai., Institute of Heteroorganic Compounds, Academy of Sciences of the USSR, Moscow, Doklady Chemistry, vol. 212, No. 4, pp. 799-800 (Oct. 1973).

* cited by examiner

METHOD FOR PRODUCING TRIALKYL GALLIUM

BACKGROUND OF THE INVENTION

1. Field of the Invention

The present invention relates to a method for producing a trialkyl gallium for use as an ingredient for forming a compound semiconductor thin film such as GaN by epitaxial crystal growth by MOCVD (metalorganic chemical vapor deposition) and like techniques.

2. Description of the Related Art

With the advancement of cellular phones and optical communication technologies, demand is rapidly growing for compound semiconductors for use in high speed electronic devices such as high electron mobility transistors (HEMTs) and heterojunction bipolar transistors (HBTs) for use in cellular phones; semiconductor lasers for use with optical communications, DVDs, etc.; optical devices such as white and blue super high-intensity LEDs for use in displays; and other applications.

In general, alkyl metals containing group IIB (group 12) and group IIIB (group 13) elements, and in particular methyl or ethyl metals, are often used as metalorganics (MOs) for use as ingredients of compound semiconductors. A great demand exists for, in particular, group IIIB gallium in the form of alkylgalliums for the production of compound semiconductors by MOCVD with group VB (group 15) elements such as nitrogen, arsenic, and the like.

A typical example of a prior-art method for producing an alkylgallium is reacting an alkyl halide with a gallium-magnesium mixture or gallium-magnesium alloy. This method is advantageous in allowing commercially readily available metallic gallium and metallic magnesium of high purity to be used as received, and in not requiring the use of a reagent for which care must be taken.

Some examples of similar methods are given below. Many prior-art methods use a gallium-magnesium alloy because the use of a gallium-magnesium alloy as a starting material results in the production of a trialkyl gallium in higher yields than the use of a gallium-magnesium mixture. U.S. Pat. No. 5,248,800 describes that the use of a gallium-magnesium alloy having a molar ratio of Mg/Ga from 1.6 to 2.4 in the reaction of a gallium-magnesium alloy and an alkyl iodide results in the production of trialkyl gallium in a high yield of 80 to 90%. Furthermore, U.S. Pat. No. 5,248,800 discloses that the yield of a trialkyl gallium with the use of a gallium-magnesium mixture is 15%. That is, this patent publication clearly states that a method that uses a gallium-magnesium alloy as a starting material produces a trialkyl gallium in a higher yield than the method using a gallium-magnesium mixture.

UK Patent No. 2123423 discloses a method for producing a trialkyl gallium in which a gallium-magnesium alloy and an alkyl iodide are reacted in the presence of an ether.

Methods using a gallium-magnesium alloy require a process of preparing an alloy by heating, and it is difficult to prepare a uniform gallium-magnesium alloy. Reports state that constant yields cannot be obtained due to this difficulty (A. C. Jones, D. J. Cole-Hamilton, A. K. Holliday, M. J. Mahmad, *J. Chem. Soc., Dalton Trans.*, 1047 (1983); K. B. Starowieski, K. J. Klabunde, *Appl. Organomet. Chem.*, 3, 219 (1989)).

Therefore, with an eye to the simplification of the production process and stable productivity, it is desirable to use a gallium-magnesium mixture, which is simpler.

In this connection, L. I. Zakharkin, V. V. Gavrilenko, N. P. Fatyushina, *Russ. Chem. Bull.*, 46, 379 (1997) discloses a method in which trimethyl gallium is directly produced by co-pulverizing a gallium-magnesium-methyl iodide mixture while heating. Moreover, this publication discloses a method for producing triethyl gallium in which a gallium-magnesium mixture and a small amount of iodine are vacuum-heated, and then reacted with ethyl iodide in the presence of hexane or in the absence of a solvent. The yield of triethyl gallium is substantially the same when a gallium-magnesium alloy or gallium-magnesium mixture is used, or when vacuum heating is conducted in the presence of hexane or in the absence of a solvent. In this publication, powdered magnesium is used.

V. I. Bregadze, L. M. Golubinskaya, B. I. Kozyrkin, *J. Clust. Sci.*, 13, 631 (2002) discloses that trimethyl gallium can be obtained in a high yield of 80 to 90% by reacting a gallium-magnesium mixture and methyl iodide in the presence of isoamyl ether. In this publication, powdered magnesium is also used.

The use of a gallium-magnesium mixture usually results in a lower yield than the use of a gallium-magnesium alloy. Attempts to obtain a high yield using a gallium-magnesium mixture limit the usable form of magnesium to powders as described in the aforementioned *Russ. Chem. Bull.*, 46, 379 (1997); and *J. Clust. Sci.*, 13, 631 (2002).

The majority of such prior-art methods use alkyl iodides, which are most reactive among the alkyl halides. Although an alkyl iodide has an advantage, i.e., high reactivity, it is likely to result in a Wurtz coupling reaction as a side reaction as shown in Reaction Formula (1) below:

$$2RI + Mg \rightarrow R-R + MgI_2 \qquad (1)$$

wherein R is an alkyl group.

Moreover, alkyl iodides are more expensive than alkyl bromides and alkyl chlorides. In addition, since the boiling point of the resulting trimethyl gallium and the boiling point of methyl iodide are close, it is difficult to isolate the trimethyl gallium for purification.

With an eye to negating such disadvantages of alkyl iodides, Japanese Unexamined Patent Publication No. 1991-123784 discloses the use of a methyl bromide and methyl iodide mixture as an alkyl halide in a method for producing trimethyl gallium in which a gallium-magnesium alloy and a methyl halide are reacted in order to reduce the total amount of methyl iodide necessary in the reaction.

Methyl bromide has a higher reactivity than methyl chloride. However, methyl bromide has been designated as an ozone-depleting substance, and the use thereof has been gradually reduced since 1999. Hence, alkyl iodides and alkyl bromides have, as described above, both advantages and disadvantages.

It is presumed that the reaction that produces trialkyl gallium, i.e., the reaction of gallium, magnesium, and alkyl halide, follows Reaction Formula (2) below:

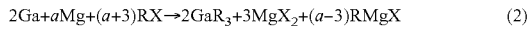

$$2Ga + aMg + (a+3)RX \rightarrow 2GaR_3 + 3MgX_2 + (a-3)RMgX \qquad (2)$$

wherein R is an alkyl group, X is a halogen atom, and a is a positive integer.

It can be deduced that an alkyl magnesium halide (RMgX), i.e., a Grignard reagent, is involved in the production of the trialkyl gallium.

The Synthesis, Reactions and Structures of Organometallic Compounds, in *Comprehensive Organometallic Chemistry*, S. G. Wilkinson, F. G. A. Stones, E. W. Abel, Eds.; Vol. 1, Pergamon Press Ltd., (1982) Chapter 4 teaches that the production of a Grignard reagent is greatly affected by the type of halogen contained in an alkyl halide and the type of reaction solvent, and that the extent of halogen reactivity is, from strongest to weakest, iodine>bromine>chlorine>fluorine.

This publication teaches that Lewis bases such as ethers and amines are usually used as reaction solvents and such solvents are likely to form adducts with trialkyl galliums, and the use of hydrocarbons as reaction solvents that barely form adducts with trialkyl galliums significantly impairs the Grignard reagent productivity.

Moreover, M. J. S. Gynane, I. J. Worral, *J. Organomet. Chem.*, 40, C59 (1972) discloses that the reactivity of alkyl halides to gallium is significantly weaker than to magnesium. This publication teaches that the extent of reactivity of alkyl halides to gallium, as with their reactivity to magnesium, is, from strongest to weakest, alkyl iodide>alkyl bromide. Although it does not refer to the reactivity of alkyl chlorides, it is presumable that the reactivity of alkyl chlorides is weaker still.

Soviet Patent Publication No. 388563 discloses a method in which an alkyl chloride is used as an alkylating agent. In this publication, a trialkyl gallium is produced by reacting an alkyl halide with a gallium-magnesium mixture or gallium-magnesium alloy in the presence of a Lewis base such as dibutyl ether, diisoamyl ether, diethyl ether, or like ether. However, the reaction using an alkyl chloride does not produce a trialkyl gallium in a satisfactory yield. No reaction of a gallium-magnesium mixture and an alkyl chloride is described in this patent publication.

Although alkyl chlorides do not have the disadvantages of alkyl iodides and alkyl bromides, alkyl chlorides are very poorly reactive with respect to gallium and magnesium. So far, no alkyl halide satisfies all requirements.

The methods described in the aforementioned publications mostly use ethers as reaction solvents. Use of ethers results in enhanced reactivity and yield; however, ethers coordinate with the resulting alkyl gallium, thereby forming an adduct. Depending on the type of ether, it is often difficult to separate ether adducts from alkyl galliums even when distillation and like techniques are used, making it difficult to produce metalorganic compounds of high purity. The use of a metalorganic compound containing ether adducts thereof as an ingredient in the production of compound semiconductors by MOCVD tends to impair the electric properties of the resulting compound semiconductors due to the presence of oxygen during crystal growth. Hence, use of ethers as solvents has, as described above, both advantages and disadvantages The aforementioned *Russ. Chem. Bull.*, 46, 379 (1997) discloses a method that does not use an ether. Although this method does not use any ether at all, purification of a trialkyl gallium to a high purity may be difficult due to the wear on grinders and grinding balls if a starting mixture is ground prior to the production of a trialkyl gallium or due to the iodine contamination if iodine is used.

Japanese Unexamined Patent Publication No. 1989-301684 discloses that, with respect to a method for producing a trialkyl gallium using a gallium-magnesium alloy, a trialkyl gallium can be produced using an ether as a reaction solvent in a less than stoichiometric amount relative to magnesium.

Japanese Unexamined Patent Publication No. 1991-127795 teaches that, with respect to a method for producing a trialkyl gallium using a gallium-magnesium alloy, a trialkyl gallium can be produced using as reaction solvents a hydrocarbon in combination with an ether in a less than stoichiometric amount relative to magnesium.

As stated above, there are prior-art methods that use hydrocarbons as reaction solvents. Hydrocarbon solvents do not have the disadvantages described above in connection with the ether solvents. However, the use of hydrocarbon solvents usually results in low reactivity and thus production of a trialkyl gallium in a poor yield, as described in the aforementioned The Synthesis, Reactions and Structures of Organometallic Compounds, in *Comprehensive Organometallic Chemistry*, S. G. Wilkinson, F. G. A. Stones, E. W. Abel, Eds.; Vol. 1, Pergamon Press Ltd., (1982), Chapter 4.

Ethers and hydrocarbons have their advantages and disadvantages as described above. So far, no solvent meets all requirements.

It is preferable to use a hydrocarbon as a solvent and an alkyl chloride as an alkyl halide to allow the resulting trialkyl gallium to be highly purified. However, the use of these compounds results in poor reactivity and yields.

The prior-art methods for producing a trialkyl gallium described above use the reaction of an alkyl halide with a gallium-magnesium mixture or gallium-magnesium alloy. Other prior-art methods for producing an alkyl gallium include (a) to (e) below:

(a) reaction of a gallium halide with a Grignard reagent (for example, U.S. Pat. No. 4,604,473);

(b) reaction of a gallium halide with a trialkyl aluminum (for example, K. K. Fukin, I. A. Frolov, *Tr. Khim. Khim. Tekhnol.*, 4, 40 (1973));

(c) reaction of a gallium halide with an alkyl lithium (for example, R. A. Kovar, H. Derr, D. Brandau, J. O. Calloway, *Inorg. Chem.*, 14, 2809 (1975));

(d) reaction of a gallium halide with a dialkyl zinc (for example, C. A. Kraus, F. E. Toonder, *Proc. Natl. Acad. Sci. USA*, 19, 292 (1933)); and (e) reaction of gallium and a dialkylmercury (for example, G. E. Coates, *J. Chem. Soc.*, 2003 (1951)).

In these methods, a gallium halide or elemental gallium is used as the gallium-containing ingredient. There is currently no method known for efficiently producing a trialkyl gallium using other gallium-containing ingredients.

BRIEF SUMMARY OF THE INVENTION

A first object of the present invention is to provide a method for producing a trialkyl gallium in an enhanced yield by the reaction of gallium, magnesium, and an alkyl halide without using a gallium-magnesium alloy.

Providing a method for producing a trialkyl gallium in an enhanced yield by the reaction of gallium, magnesium, and an alkyl chloride without using a gallium-magnesium alloy is encompassed within the first object of the invention.

Furthermore, providing a method for producing a trialkyl gallium in an enhanced yield by the reaction of gallium, magnesium, and an alkyl halide using a hydrocarbon as a reaction solvent without using a gallium-magnesium alloy is encompassed within the first object.

Furthermore, the first object of the invention includes providing a method for producing a trialkyl gallium in an enhanced yield by the reaction of gallium, magnesium, and an alkyl halide when a hydrocarbon is used as a solvent, an alkyl chloride is used as the alkyl halide, and no gallium-magnesium alloy is used.

A second object of the present invention is to provide a method for producing a trialkyl gallium in an enhanced yield in which a novel gallium-containing ingredient is used in the production of a trialkyl gallium.

The inventors conducted extensive research to achieve the objects described above, and found the following.

(i) A trialkyl gallium can be produced in an enhanced yield by reacting gallium, magnesium, and at least one alkyl halide in at least one ether; and diluting the reaction system with at least one ether during the reaction.

(ii) A trialkyl gallium can be produced in an enhanced yield by preactivating a mixture of magnesium and molten gallium by heating it in a vacuum, and then reacting the vacuum-heated mixture and at least one alkyl chloride in at least one ether.

(iii) A trialkyl gallium can be produced in an enhanced yield by preactivating a mixture of magnesium and molten gallium by heating it in a vacuum, and reacting the vacuum-heated mixture and at least one alkyl halide selected from the group consisting of alkyl iodides and alkyl bromides in at least one hydrocarbon.

(iv) A trialkyl gallium can be produced in an enhanced yield by preactivating a mixture of magnesium and molten gallium by heating it in a vacuum, and reacting the vacuum-heated mixture and at least one alkyl chloride in at least one hydrocarbon.

(v) A trialkyl gallium can be produced in an enhanced yield by reacting at least one alkyl metal used as an alkylating agent and at least one alkyl gallium halide represented by General Formula (3):

$$Ga_2R_mX_{6-m} \qquad (3)$$

wherein R is a methyl or ethyl group, X is a halogen atom, and m is an integer from 1 to 5.

The present invention was accomplished based on the findings described above and provides methods for producing a trialkyl gallium as presented below.

1. A method for producing a trialkyl gallium comprising the steps of:
reacting gallium, magnesium, and at least one alkyl halide in at least one ether to produce a trialkyl gallium; and
diluting during the reaction the reaction system with at least one ether.

2. The method according to item 1, wherein the reaction system has a magnesium content of 5 mol/l or greater at the beginning the reaction, and the reaction system is diluted to have a total magnesium content of 4 mol/l or less.

3. The method according to item 1, wherein gallium, magnesium, and at least one alkyl halide are reacted by introducing at least one alkyl halide into a mixture of gallium, magnesium, and at least one ether.

4. The method according to item 3, wherein at least one alkyl halide is introduced dropwise into the mixture of gallium, magnesium, and at least one ether.

5. The method according to item 1, wherein the reaction system is diluted within about 30 minutes of when an alkyl magnesium halide and magnesium halide precipitate from the reaction system and the temperature increase of the reaction system has ceased (Ts).

6. The method according to item 1, wherein 1 to 10 mol of magnesium is used per mol of gallium.

7. The method according to item 1, wherein magnesium is in the form of ribbons, shavings, chips, or grains.

8. The method according to item 1, wherein the at least one alkyl halide is at least one member selected from the group consisting of alkyl iodides and alkyl bromides.

9. The method according to item 1, wherein the at least one alkyl halide contains a $C_{1-10}$ alkyl group.

10. A trialkyl gallium obtained according to the method of item 1.

11. A gallium-based compound semiconductor device furnished with a gallium-based compound semiconductor thin film created by epitaxial growth using as starting materials the trialkyl gallium of item 10 and at least one group VB (group 15) element-containing compound selected from the group consisting of nitrogen-containing compounds, phosphorus-containing compounds, and arsenic-containing compounds.

12. A method for producing a trialkyl gallium comprising the steps of:
heating in a vacuum a mixture of magnesium and molten gallium, and
reacting the vacuum-heated mixture with at least one alkyl halide in at least one solvent to produce a trialkyl gallium.

13. The method according to item 12, wherein the at least one solvent is an ether and the at least one alkyl halide is an alkyl chloride.

14. The method according to item 13, wherein the vacuum heating is performed at 1000 Pa or less and at 60° C. or higher.

15. The method according to item 13 further comprising the step of maintaining the magnesium and molten gallium in a mixed state,
the step being performed prior to the step of vacuum heating.

16. The method according to item 15, wherein the step of maintaining the magnesium and molten gallium in a mixed state is performed at 40 to 60° C.

17. The method according to item 13, wherein 1 to 10 mol of magnesium is used per mol of gallium.

18. The method according to item 13, wherein the at least one alkyl chloride contains a $C_{1-10}$ alkyl group.

19. A trialkyl gallium obtained according to the method of item 13.

20. A gallium-based compound semiconductor device furnished with a gallium-based compound semiconductor thin film created by epitaxial growth using as starting materials the trialkyl gallium of item 19 and at least one group VB (group 15) element-containing compound selected from the group consisting of nitrogen-containing compounds, phosphorus-containing compounds, and arsenic-containing compounds.

21. The method according to item 12, wherein the at least one solvent is a hydrocarbon, and the at least one alkyl halide is selected from the group consisting of alkyl iodides and alkyl bromides.

22. The method according to item 21, wherein the vacuum heating is performed at 1000 Pa or less and at 60° C. or higher.

23. The method according to item 21 further comprising the step of maintaining the magnesium and molten gallium in a mixed state,
the step being performed prior to the step of vacuum heating.

24. The method according to item 23, wherein the step of maintaining the magnesium and molten gallium in a mixed state is performed at 40 to 60° C.

25. The method according to item 21, wherein 1 to 20 mol of magnesium is used per mol of gallium.

26. The method according to item 21, wherein the at least one alkyl halide contains a $C_{1-10}$ alkyl group.

27. A trialkyl gallium obtained according to the method of item 21.

28. A gallium-based compound semiconductor device furnished with a gallium-based compound semiconductor thin film created by epitaxial growth using as starting materials the trialkyl gallium of item 27 and at least one group VB (group 15) element-containing compound selected from the group consisting of nitrogen-containing compounds, phosphorus-containing compounds, and arsenic-containing compounds.

29. The method according to item 12, wherein the at least one solvent is a hydrocarbon, and the at least one alkyl halide is an alkyl chloride.

30. The method according to item 29, wherein the vacuum heating is performed at 1000 Pa or less and at 60° C. or higher.

31. The method according to item 29 further comprising the step of maintaining the magnesium and molten gallium in a mixed state, the step being performed prior to the step of vacuum heating.

32. The method according to item 31, wherein the step of maintaining the magnesium and molten gallium in a mixed state is performed at 40 to 60° C.

33. The method according to item 29, wherein 1 to 10 mol of magnesium is used per mol of gallium.

34. The method according to item 29, wherein the alkyl chloride contains a $C_{1-10}$ alkyl group.

35. A trialkyl gallium obtained according to the method of item 29.

36. A gallium-based compound semiconductor device furnished with a gallium-based compound semiconductor thin film created by epitaxial growth using as starting materials trialkyl gallium of item 35 and at least one group VB (group 15) element-containing compound selected from the group consisting of nitrogen-containing compounds, phosphorus-containing compounds, and arsenic-containing compounds.

37. A method for producing a trialkyl gallium comprising the step of reacting at least one alkyl metal with at least one alkylgallium halide represented by General Formula (3):

$$Ga_2R_mX_{6-m} \qquad (3)$$

wherein R is a methyl or ethyl group, X is a halogen atom, and m is an integer from 1 to 5, to produce a trialkyl gallium.

38. The method according to item 37, wherein the at least one alkyl metal is at least one compound selected from the group consisting of lithium-containing compounds, magnesium-containing compounds, aluminium-containing compounds, and zinc-containing compounds.

39. The method according to item 37, wherein the at least one alkyl metal is at least one compound selected from the group consisting of alkyl lithium compounds, alkyl magnesium halides, trialkyl aluminum compounds, and dialkyl zinc compounds.

40. The method according to item 37, wherein the at least one alkyl metal is at least one compound selected from the group consisting of methyl metal compounds and ethyl metal compounds.

41. The method according to item 37, wherein the at least one alkyl metal is used in an amount of 0.5 to 2 times the stoichiometric amount calculated relative to the compound represented by General Formula (3).

42. A trialkyl gallium obtained according to the method of item 37.

43. A gallium-based compound semiconductor device furnished with a gallium-based compound semiconductor thin film created by epitaxial growth using as starting materials the trialkyl gallium of item 42 and at least one group VB (group 15) element-containing compound selected from the group consisting of nitrogen-containing compounds, phosphorus-containing compounds, and arsenic-containing compounds.

According to the methods recited in items 1 to 9 (hereinafter collectively referred to as method 1), a trialkyl gallium can be produced in an enhanced yield, without using a gallium-magnesium alloy, by reacting an alkyl halide with a gallium-magnesium mixture, which is simpler, thereby obviating complex alloy production and enabling a trialkyl gallium to be produced in a consistent and enhanced yield.

With respect to method 1, without using magnesium in the form of a powder, high reactivity can be attained with magnesium in the form of shavings or chips, which are easier to handle, resulting in an enhanced yield.

Therefore, the first object of the present invention can be achieved by method 1 of the present invention.

According to the methods recited in items 13 to 18 (hereinafter collectively referred to as the first aspect of method 2), a trialkyl gallium can be produced in an enhanced yield using an alkyl chloride as an alkylating agent, which is generally considered to be poorly reactive, during the reaction of gallium, magnesium, and an alkyl halide.

A trialkyl gallium produced using an alkyl chloride can be processed to a higher purity than a trialkyl gallium produced using an alkyl iodide or alkyl bromide. Moreover, due to their broad usage, alkyl chlorides are readily available.

Usually, compared with the use of a gallium-magnesium alloy, the use of a gallium-magnesium mixture results in a trialkyl gallium in a smaller yield. However, according to the first aspect of method 2, a trialkyl gallium can be produced in an enhanced yield merely by using gallium and magnesium together in place of a gallium-magnesium alloy whose production is complex.

Therefore, the first object of the present invention can be also achieved by the first aspect of method 2 of the present invention.

According to the methods recited in items 21 to 26 (hereinafter collectively referred to as the second aspect of method 2), an alkyl gallium can be produced in a hydrocarbon, which usually greatly reduces reactivity, in a yield sufficient for practical use, due to preactivation of the gallium and magnesium.

In the second aspect of method 2, a hydrocarbon solvent is used as a reaction solvent, and no trialkyl gallium hydrocarbon adduct or oxygen atoms derived from conventionally used ether solvents are present, thereby allowing the production of a trialkyl gallium of high purity after purification. Therefore, the second aspect of method 2 is advantageous for producing a trialkyl gallium as an MOCVD ingredient in the production of compound semiconductors with enhanced electrical properties.

A prior-art activation method is vacuum-heating a gallium-magnesium alloy in the presence of iodine (L. I. Zakharkin, V. V. Gavrilenko, N. P. Fatyushina, *Russ. Chem. Bull.*, 46, 379 (1997)). The use of a reaction enhancer such as iodine makes it difficult to produce a trialkyl gallium of high purity due to the contamination thereby. In contrast, in the second aspect of method 2, gallium and magnesium are activated without such a reaction enhancer, thereby making it easy to produce a trialkyl gallium of high purity.

Usually, compared with the use of a gallium-magnesium alloy, the use of a gallium-magnesium mixture results in a trialkyl gallium in a smaller yield. However, according to the second aspect of method 2, a trialkyl gallium can be produced in an enhanced yield without complex alloy production. Furthermore, it is difficult using prior-art methods to produce a trialkyl gallium in a consistent yield when such an alloy is used, but according to the second aspect of method 2, a trialkyl gallium can be produced in a consistent and enhanced yield.

Therefore, the first object of the present invention can also be achieved by the second aspect of method 2.

According to the methods recited in items 29 to 34 (hereinafter collectively referred to as the third aspect of method 2), an alkyl gallium can be produced in an enhanced yield despite using a hydrocarbon solvent and an alkyl chloride, both of which usually greatly reduce reactivity, due to preactivation of the gallium and magnesium.

A trialkyl gallium produced using an alkyl chloride can be processed to a higher purity than a trialkyl gallium produced using an alkyl iodide or alkyl bromide. Moreover, due to their broad usage, alkyl chlorides are readily available.

In the third aspect of method 2, a hydrocarbon solvent is used as a reaction solvent, and no trialkyl gallium hydrocarbon adduct or oxygen atoms derived from conventionally used ether solvents are present, thereby allowing the production of a trialkyl gallium of high purity after purification. Therefore, the third aspect of method 2 is advantageous for producing a trialkyl gallium as an MOCVD ingredient in the production of compound semiconductors with enhanced electrical properties.

A prior-art activation method is vacuum-heating a gallium-magnesium alloy in the presence of iodine (L. I. Zakharkin, V. V. Gavrilenko, N. P. Fatyushina, *Russ. Chem. Bull.*, 46, 379 (1997)). The use of a reaction enhancer such as iodine makes it difficult to produce a trialkyl gallium of high purity. In contrast, in the third aspect of method 2, gallium and magnesium are activated without such a reaction enhancer, making it easy to produce a trialkyl gallium of high purity.

Usually, compared with the use of a gallium-magnesium alloy, the use of a gallium-magnesium mixture results in a trialkyl gallium in a poor yield. However, according to the third aspect of method 2, a trialkyl gallium can be produced in an enhanced yield without complex alloy production. Furthermore, it is usually difficult using prior-art methods to produce a trialkyl gallium in a consistent yield when such an alloy is used, but according to the third aspect of method 2, a trialkyl gallium can be produced in a consistent and enhanced yield.

Therefore, the first object of the present invention can also be achieved by the third aspect of method 2 of the present invention. The third aspect of method 2 greatly contributes to simplifying the production process and the stable production of a trialkyl gallium.

According to the methods recited in items 37 to 41 (hereinafter collectively referred to as method 3), a trialkyl gallium can be produced in a practically sufficient yield by simply alkylating with an alkyl metal an alkylgallium halide of General Formula (3), which heretofore has not been used.

Therefore, the second object of the present invention can be achieved by method 3 of the present invention. These methods are novel for trialkyl gallium production.

DETAILED DESCRIPTION OF THE INVENTION (I) Method 1

Method 1 of the present invention is described below in detail. Method 1 for producing a trialkyl gallium of the present invention comprises the steps of reacting gallium, magnesium, and at least one alkyl halide in at least one ether to produce a trialkyl gallium; and diluting the reaction system with at least one ether during the reaction.

Starting Materials

<Gallium>

Gallium may be a commercially available product having a purity of 99.9% (3N) or better. Commercially available gallium has a purity of up to 7N.

The electrical properties and optical properties of a compound semiconductor produced by MOCVD are greatly affected by the purity of the starting organometallic compound. Therefore, it is desirable that a trialkyl gallium of high purity be produced. Since the purity of the resulting trialkyl gallium is affected by the purity of the starting gallium, it is preferable to use gallium of high purity.

The purity of gallium is preferably 99.999% (5N) or better, and particularly preferably 99.9999% (6N) or better. High-purity gallium having a purity of 5N or better is commercially available as described above. Such gallium can be also obtained by purifying by, e.g., recrystallization, reduced pressure purification, electrolytic refining, etc., a commercially available product already having a purity of 3N or 4N.

<Magnesium>

Magnesium may be a commercially available product having a purity of 99% (2N) to 99.9999% (6N). Magnesium having a purity of 5N or better is very expensive, and therefore magnesium having a purity of 2N to 4N may be used after being purified according to vacuum distillation, vacuum sublimation, etc. In method 1 of the present invention, the purity of magnesium is preferably 3N or better.

The form of magnesium is not limited. Magnesium for use may be in the form of ribbons, shavings, chips (those smaller than shavings), powders, grains, and the like that are usually selected in the production of Grignard reagents. Powdered magnesium herein refers to having a mean particle diameter of 500 µm or less. Mean particle diameter herein is measured according to laser diffractometry.

In general, the reactivity of powdered magnesium to an alkyl halide is greater than the reactivity of magnesium that takes a bulkier form. However, according to method 1 of the present invention, high reactivity can be obtained using magnesium that takes a form other than powdered. Although care must be taken to handle and store powdered magnesium, powdered magnesium need not be used in method 1 of the present invention. Therefore, magnesium in the form of ribbons, shavings, chips, or grains is preferable. In particular, magnesium in the form of shavings or chips is preferable for their reactivity to alkyl halides and for ease of handling.

The surface of magnesium is more or less coated with an oxide film. A thick oxide film extends the induction period of the reaction. Therefore, magnesium is usually mechanically stirred, pulverized, combined with a small amount of iodine or bromine, washed with diluted hydrochloric acid, or subjected to a similar treatment prior to the reaction to activate the surface. Moreover, another method practiced for magnesium activation is adding a small amount of methyl iodide, ethyl iodide, 1,2-dibromoethane, or the like (D. E. Peason, D. Cowan, J. D. Beckler, *J. Org. Chem.*, 24, 504 (1959)). According to method 1, magnesium shows sufficient reactivity without such activation treatment, but the reaction time can be further shortened by performing such activation treatment prior to reaction.

<Solvents>

Ethers usable herein are not limited. Those that are commonly used for the production of trialkyl galliums may be used, for example, diethyl ether, di-n-propyl ether, diisopropyl ether, di-n-butyl ether, diisobutyl ether, di-sec-butyl ether, diisopentyl ether (diisoamyl ether), and like aliphatic ethers; and anisole, methylanisole, benzyl methyl ether, ethylanisole, dimethylanisole, isopropylanisole, phenetole, and like aromatic ethers.

Ethers form an adduct with the resulting trialkyl gallium. Therefore, it is preferable to isolate the trialkyl gallium by distillation to thermally decompose the ether adduct, as described below. In this connection, the ether used preferably has a higher boiling point than the trialkyl gallium. Moreover, when the thermal decomposition temperature of a trialkyl gallium ether adduct is higher than that of the trialkyl gallium, the thermal decomposition of the ether adduct is accompanied by decomposition of the trialkyl gallium. Therefore, it is preferable to select an ether such that the thermal decomposition temperature of the ether adduct is lower than that of the resulting trialkyl gallium.

Ethers may be used singly or as a combination of two or more kinds. It is preferable to use a single ether to ease purification of the resulting trialkyl gallium.

<Alkyl Halides>

Alkyl halides for use are usually those that have a $C_{1-10}$ alkyl group, and preferably a $C_{1-4}$ alkyl group. Alkyl halides having an alkyl group with an aforementioned number of carbon atom(s) are highly reactive. The use of such an alkyl halide enables the production of a trialkyl gallium that is sufficiently volatile for an MOCVD ingredient.

Alkyl chlorides, alkyl bromides, and alkyl iodides may be used. Alkyl bromides and alkyl iodides are preferable for their relatively high reactivity.

Specific examples of alkyl halides having a $C_{1-4}$ alkyl group are methyl chloride, ethyl chloride, n-propyl chloride, isopropyl chloride, n-butyl chloride, isobutyl chloride, sec-butyl chloride, tert-butyl chloride, and like alkyl chlorides; methyl bromide, ethyl bromide, n-propyl bromide, isopropyl bromide, n-butyl bromide, isobutyl bromide, sec-butyl bromide, tert-butyl bromide, and like alkyl bromides; and methyl iodide, ethyl iodide, n-propyl iodide, isopropyl iodide, n-butyl iodide, isobutyl iodide, sec-butyl iodide, tert-butyl iodide, and like alkyl iodides. Among such examples, methyl bromide, ethyl bromide, n-propyl bromide, isopropyl bromide, n-butyl bromide, isobutyl bromide, sec-butyl bromide, tert-butyl bromide, and like alkyl bromides; and methyl iodide, ethyl iodide, n-propyl iodide, isopropyl iodide, n-butyl iodide, isobutyl iodide, sec-butyl iodide, tert-butyl iodide, and like alkyl iodides are preferable.

Alkyl halides may be used singly or as a combination of two or more kinds. When two or more kinds of alkyl halides are used in combination, alkyl halides having different kinds of halogen atom or having different kinds of alkyl group may be used.

Proportions

It is presumed that the reaction that produces trialkyl gallium, i.e., the reaction of a gallium-magnesium mixture and an alkyl halide, follows Reaction Formula (2) below:

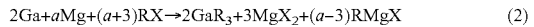

$$2Ga + aMg + (a+3)RX \rightarrow 2GaR_3 + 3MgX_2 + (a-3)RMgX \quad (2)$$

wherein R is an alkyl group, X is a halogen atom, and a is a positive integer.

It can be deduced that an alkyl magnesium halide (RMgX), i.e., a Grignard reagent, is involved in the production of the trialkyl gallium.

The molar ratio of magnesium to gallium is preferably about 1 to about 10 mol of magnesium per mol of gallium, more preferably about 1 to about 5 mol, and particularly preferably about 1 to about 3 mol. With a molar ratio being within such a range, the reaction of gallium, magnesium, and an alkyl halide can efficiently proceed to a practically sufficient extent, and a trialkyl gallium can be produced in an enhanced yield.

Stoichiometrically, by reference to Reaction Formula (2), $(a+3)/2$ mol of alkyl halide is necessary per mol of gallium and $a/2$ mol of magnesium to produce a trialkyl gallium, and the amount of alkyl halide thus varies according to the amount of gallium and the molar ratio of gallium to magnesium. The amount of alkyl halide is usually about 50 to about 200% of $(a+3)/2$ mol, and preferably about 70 to about 150% of $(a+3)/2$ mol. With an amount being within such a range, a trialkyl gallium can be obtained in an enhanced yield.

Synthesizing Reaction process

The reaction of method 1 of the present invention is carried out in an inert gas atmosphere such as nitrogen, helium, neon, argon, krypton, xenon, etc. The purity of such an inert gas is preferably 99.99% (4N) or better, and particularly preferably 99.9999% (6N) or better.

It is desirable to use an atmosphere gas from which moisture and oxygen have been removed as much as possible because moisture and oxygen present in an atmosphere gas result in not only an impaired trialkyl gallium yield but also in purity compromise. The atmosphere gas preferably has a dew point of –80° C. or lower and an oxygen content of 100 ppb or less, and particularly preferably a dew point of –100° C. or lower and an oxygen content of 10 ppb or less. Such a highly pure inert gas can be obtained by membrane separation, catalytic reaction, fluid rectification, PSA (pressure swing adsorption), etc.

The reaction is carried out by introducing gallium, magnesium, an alkyl halide, and an ether into a reaction vessel filled with an inert gas. The order of introduction the compounds into the reaction vessel is not limited. For ease of introduction into a reaction vessel, it is advantageous to introduce gallium, magnesium, ether, and then alkyl halide. In this case, it is preferably to slowly introduce the alkyl halide, and dropwise introduction is especially preferable.

A feature of method 1 of the present invention is diluting the reaction system with an ether during the reaction. The ether used for dilution may be of the same kind as the ether present in the reaction system or of a different kind. An ether of the same kind is preferable.

With respect to method 1 of the present invention, the magnesium content in the reaction system at the beginning of the reaction is usually controlled to 5 mol/l or greater, preferably 6 mol/l or greater, and more preferably 7 mol/l or greater. This is to create a magnesium-rich reaction system to securely initiate and advance the reaction of magnesium, gallium, and alkyl halide. Excessively high magnesium contents are accompanied by intense heat generation, thereby making stirring difficult. Therefore, the upper limit of the magnesium content at the beginning of the reaction is usually about 10 mol/l.

It is preferable to control by dilution the total magnesium content of the reaction system to 4 mol/l or less, and more preferably 3 mol/l or less. Excessively low magnesium contents keep the reaction from advancing smoothly, and therefore the lower limit of the total magnesium content of the reaction system after dilution is about 0.1 mol/l. The term "total magnesium content" refers to the total amount of magnesium present in the form of elemental magnesium, magnesium halide, and alkyl magnesium halide.

Dilution may be performed by introducing an ether either at once or slowly.

As the reaction progresses, supersaturated alkyl magnesium halide and by-product magnesium halide precipitate, and then dilution may be performed by introducing an ether into the reaction system. In particular, as precipitation progresses, the temperature increase of the reaction system ceases. It is preferable to perform dilution within about 30 minutes of when the temperature increase has ceased (Ts), and more preferably within about 20 minutes of Ts. In other words, it is preferable to perform dilution within about Ts±30 minutes, and more preferably within about Ts±20 minutes.

When an alkyl halide is gradually added to a mixture of gallium, magnesium and an ether, the temperature of the reaction system increases due to the addition of the alkyl halide. Further addition of the alkyl halide causes alkyl magnesium halide and magnesium halide to precipitate, and the temperature increase comes to a halt. Ether is then introduced into the reaction system for dilution.

The reaction temperature is suitably selected to efficiently carry out the reaction in consideration of the type of ether and alkyl halide used and other factors. When gallium, magnesium, ether, and alkyl halide are mixed, the temperature of the reaction system increases; the temperature increase ceases as precipitation progresses; and the temperature increases again as the reaction system is diluted. Thereafter, the reaction is continued while controlling the temperature of the reaction system to usually within about 0 to about 200° C., preferably about 40 to about 160° C., and more preferably about 60 to about 120° C. When alkyl halide is added gradually, the reaction is carried out within an aforementioned temperature range after the entire alkyl halide is added.

About 3 to about 30 hours of reaction within an aforementioned temperature range produces a trialkyl gallium.

Furthermore, the reaction pressure is not limited, and the reaction can be carried out under atmospheric pressure, under reduced pressure, or under increased pressure.

Purification Process

Crude trialkyl gallium obtained after the reaction includes ether adducts and alkyl halide adducts of trialkyl gallium. Therefore, the reaction solution is subjected to distillation to decompose such adducts. That is, the trialkyl gallium is isolated according to fractional distillation. It is preferable that the heating temperature is lower than the thermal decomposition temperature of the trialkyl gallium and higher than the thermal decomposition temperatures of ether adducts and alkyl halide-adducts of the trialkyl gallium. Distillation may be carried out under atmospheric pressure or reduced pressure.

Further purification such as precision distillation, sublimation, etc., can be performed, thereby giving a trialkyl gallium having a purity of at least 99.999% (5N) that can be used as an MOCVD ingredient.

This purification process is usually performed in an inert gas atmosphere.

(II) Method 2

Method 2 of the present invention is described below in detail. Method 2 for producing a trialkyl gallium of the present invention comprises a first step of heating in a vacuum a mixture of magnesium and molten gallium and a second step of reacting the vacuum-heated mixture with at least one alkyl halide in at least one solvent to produce a trialkyl gallium.

Methods encompassed within method 2 are described below as first to third aspects.

(1) First Aspect

The first aspect of method 2 of the present invention is described below in detail. A method for producing a trialkyl gallium encompassed within the first aspect comprises a first step of heating in a vacuum a mixture of magnesium and molten gallium and a second step of reacting the vacuum-heated mixture with at least one alkyl chloride in at least one ether to produce a trialkyl gallium.

Starting Materials

<Gallium>

Gallium is as described above in connection with method 1.

<Magnesium>

Purity of magnesium is as described above in connection with method 1.

The form of magnesium is not limited. Magnesium for use may be in the form of ribbons, shavings, chips (those smaller than shavings), powders, grains, and the like that are usually selected for the production of Grignard reagents. Powdered magnesium herein refers to having a mean particle diameter of 500 μm or less. Mean particle diameter herein is measured according to laser diffractometry.

In the first aspect in particular, magnesium in the form of shavings, chips, powders, or grains that pass through a mesh sieve with an aperture size of 2 mm (JIS Z8801) is preferable. Magnesium that cannot pass through such a mesh sieve with an aperture size of 2 mm may be subjected to pulverization, grinding, or the like to be able to pass through such a mesh sieve with an aperture size of 2 mm prior to application to a method encompassed within the first aspect. Magnesium that passes through a mesh sieve with an aperture size of 2 mm herein refers to magnesium such that at least 99 wt. % of it passes through such a mesh sieve. Moreover, it is more preferable to use powdered magnesium having a mean particle diameter of 500 μm or less. Mean particle diameter herein is measured according to laser diffractometry. Use of magnesium having such a size enhances reactivity and yield.

The reactivity of magnesium to an alkyl halide is proportional to the specific surface area of the magnesium. It is therefore advantageous to use powdered magnesium having a specific surface area of 0.1 m$^2$/g or greater, and particularly 1 m$^2$/g or greater. To ensure sufficient reactivity and ease of handling, the lower limit of the specific surface area is usually about 0.1 m$^2$/g. Specific surface area herein is measured according to the BET method.

<Solvents>

Usable ethers are as described above in connection with method 1.

<Alkyl Chlorides>

Alkyl chlorides for use are usually those that have a $C_{1-10}$ alkyl group, and preferably a $C_{1-4}$ alkyl group. Alkyl chlorides having an alkyl group with an aforementioned number of carbon atom(s) are highly reactive. The use of such an alkyl chloride enables the production of a trialkyl gallium that is sufficiently volatile for an MOCVD ingredient.

Specific examples of alkyl chlorides having a $C_{1-4}$ alkyl group are methyl chloride, ethyl chloride, n-propyl chloride, isopropyl chloride, n-butyl chloride, isobutyl chloride, sec-butyl chloride, and tert-butyl chloride. Among these examples, methyl chloride and ethyl chloride having a $C_{1-2}$ alkyl group are particularly preferable. Alkyl chlorides may be used singly or as a combination of two or more kinds.

In view of Reaction Formula (2) above, it is presumed that the reaction that produces trialkyl gallium, i.e., the reaction of gallium, magnesium and alkyl chloride, follows Reaction Formula (4) below:

$$2Ga + aMg + (a+3)RCl \rightarrow 2GaR_3 + 3MgCl_2 + (a-3)RMgCl \quad (4)$$

wherein R is an alkyl group, and a is a positive integer.

The molar ratio of magnesium to gallium is preferably about 1 to about 10 mol of magnesium per mol of gallium, more preferably about 1 to about 5 mol, and particularly preferably about 1 to about 3 mol. With a molar ratio being within such a range, the reaction of gallium, magnesium, and an alkyl chloride can efficiently proceed to a practically sufficient extent, and trialkyl gallium can be produced in an enhanced yield.

Stoichiometrically, by reference to Reaction Formula (4), (a+3)/2 mol of alkyl chloride is necessary per mol of gallium and a/2 mol of magnesium to produce a trialkyl gallium, and the amount of alkyl chloride thus varies according to the amount of gallium and the molar ratio of gallium to magnesium. The amount of alkyl chloride is usually about 50 to about 200% of (a+3)/2 mol, and preferably about 70 to about 150% of (a+3)/2 mol. With an amount being within such a range, a trialkyl gallium can be obtained in an enhanced yield.

First Step (Preactivation Process)

The surface of magnesium is more or less coated with an oxide film, and the oxide film extends the induction period of the reaction. Therefore, magnesium is usually mechanically stirred, pulverized, combined with a small amount of iodine or bromine, washed with diluted hydrochloric acid, or subjected to a similar treatment prior to the reaction, to activate the surface. Another method practiced for magnesium activation is a entrainment method in which a small amount of methyl iodide, ethyl iodide, 1,2-dibromoethane, or the like is added (D. E. Peason, D. Cowan, J. D. Beckler, *J. Org. Chem.*, 24, 504 (1959)).

However, a practically sufficient reactivity cannot be obtained from such activation procedures, e.g., mechanical stirring, pulverization, and washing with diluted hydrochloric acid. Moreover, although the method of adding iodide, 1,2-dibromoethane, or a like reaction accelerator is effective in accelerating the reaction, impurities derived from such a reaction accelerator contaminate the resulting trialkyl gallium, thereby impairing the purity of the trialkyl gallium. Furthermore, entrainment method, since it involves activation, requires magnesium in a greater amount. Therefore, the aforementioned prior-art preactivation methods are hardly usable in producing trialkyl galliums of high purity for use as MOCVD ingredients in compound semiconductor production.

In the first aspect of method 2, gallium and magnesium are subjected to preactivation prior to the reaction with an alkyl chloride. That is, a mixture of magnesium and molten gallium is heated in a vacuum. This preactivation contributes not only to the removal of moisture present on the surface of the gallium and magnesium and to the production of an alkyl magnesium chloride but also to uniform mixing of the gallium and magnesium. The reactivity of an alkyl chloride to gallium is weaker than to magnesium so that this preactivation is considered effective with gallium as well as magnesium.

A mixture of magnesium and molten gallium may be prepared by mixing gallium and magnesium and then heating the mixture to a temperature higher than the melting point of gallium (29.8° C.), or mixing magnesium and already molten gallium.

Prior to preactivation by vacuum stirring, a mixture of molten gallium and magnesium may be left to stand for a while at a temperature at which gallium becomes sufficiently molten, i.e. the magnesium and molten gallium are maintained in a mixed state, thereby enabling activation to be performed more efficiently. The temperature to maintain the mixed state is preferably 40° C. or higher, and more preferably 50° C. or higher. With a temperature being within such a range, gallium can be maintained in a molten state, thereby enabling sufficient activation. Overly high temperatures do not produce any extra effect, and therefore a sufficient upper limit of the heating temperature is usually about 60° C. In this instance, the temperature need not be kept constant.

The pressure conditions for maintaining the mixed state are not limited. Usually, atmospheric pressure is sufficient. The duration of maintaining the mixed state is not limited, and is usually at least 30 minutes, and preferably at least 1 hour. Activation can sufficiently progress given such periods. Maintaining the mixed state for about 3 hours is sufficient.

The vacuum conditions during vacuum heating a mixture of magnesium and molten gallium are not limited. The vacuum heating is usually performed at 1000 Pa or less, preferably 100 Pa or less, and more preferably 10 Pa or less. With a degree of vacuum being within an aforementioned range, moisture and the like present on the surface of gallium and magnesium can be sufficiently removed, thereby enabling a trialkyl gallium to be produced in an enhanced yield. Overly high degrees of vacuum do not produce any extra effect, and therefore a sufficient upper limit of the degree of vacuum is usually about $10^{-6}$ Pa.

The temperature during vacuum heating is usually about 60° C. or higher, preferably 80° C. or higher, and more preferably 110° C. or higher. With a temperature within an aforementioned range, moisture and the like present on the surface of magnesium can be sufficiently removed, thereby enabling gallium and magnesium to come into contact sufficiently. Excessively high temperatures do not produce any extra effect, and therefore a sufficient upper limit of the temperature is usually about 200° C.

The duration of vacuum heating is not limited, and is usually at least 1 hour, and preferably at least 3 hours. About 5 hours of vacuum heating is sufficient.

During vacuum heating and during maintaining magnesium and molten gallium in a mixed state, if it is performed, the mixture may be left to stand as is or may be stirred. For efficient activation, it is advantageous to perform stirring. Stirring can be performed according to known methods, e.g., stirring using a magnetic stirrer, inductive stirring, and like techniques. Stirring can progress smoothly by adding liquid paraffin, vaseline oil or the like to the mixture during stirring.

The optional maintenance of the mixed state of magnesium and molten gallium, and vacuum heating are all performed in an inert gas atmosphere such as nitrogen, helium, neon, argon, krypton, xenon, etc. The purity of an inert gas is preferably 99.99% (4N) or better, and particularly preferably 99.9999% (6N) or better.

It is desirable to use an atmosphere gas from which moisture and oxygen have been removed as much as possible because moisture and oxygen present in an atmosphere gas result in not only an impaired trialkyl gallium yield but also in purity compromise. The atmosphere gas preferably has a dew point of −80° C. or lower and an oxygen content of 100 ppb or less, and particularly preferably a dew point of −100° C. or lower and an oxygen content of 10 ppb or less. Such a highly pure inert gas can be obtained by membrane separation, catalytic reaction, fluid rectification, PSA (pressure swing adsorption), etc.

Second Step (Synthesizing Reaction Process)

In the first aspect of method 2, the synthesizing reaction is carried out in an aforementioned inert gas atmosphere. Moisture and oxygen present in a gas atmosphere should be removed as described above.

The synthesizing reaction is carried out by introducing an activated gallium-magnesium mixture, an ether, and at least one alkyl chloride into a reaction vessel filled with an inert gas. In particular, for ease of introduction into the reaction vessel, it is advantageous to introduce in the order of gallium-magnesium mixture and ether, and then slowly alkyl chloride into the reaction vessel.

The amount of ether is not limited. It is preferably such that the gallium content and the magnesium content in the solvent at the beginning of the reaction (the gallium content and the magnesium content independently refer to molar amounts per liter of solvent) are both independently about 0.01 to about 10 mol/l, and more preferably about 0.1 to about 5 mol/l. With contents being within such a range, the reactivity of the ingredients can be sufficiently enhanced, resulting in an enhanced trialkyl gallium yield, while the reaction can be easily controlled. That is, sudden and excessive advancement of the reaction, untimely termination of the reaction due to precipitation of alkyl magnesium chloride, and difficulty of stirring due to by-product magnesium chloride do not occur.

The reaction temperature is suitably selected to efficiently carry out the reaction in consideration of the type of ether and alkyl halide used and other factors. When a gallium-magnesium mixture, ether, and alkyl chloride are mixed, the temperature of the reaction solution increases. After mixing the compounds, especially after introducing all of the alkyl chloride, the reaction is carried out while controlling the temperature of the reaction solution usually within about 0 to about 200° C., preferably about 40 to about 160° C., and more preferably about 60 to about 120° C. Usually, 3 to 30 hours of reaction produces a trialkyl gallium.

Furthermore, the synthesizing reaction pressure is not limited, and the reaction can be carried out under atmospheric pressure, under reduced pressure, or under increased pressure.

Purification Process

The purification process is as described in connection with method 1.

(2) Second Aspect

The second aspect of method 2 of the present invention is described below in detail. A method for producing a trialkyl gallium encompassed within the second aspect comprises a first step of heating in a vacuum a mixture of magnesium and molten gallium and a second step of reacting the vacuum-heated mixture with at least one alkyl halide selected from the group consisting of alkyl iodides and alkyl bromides in at least one hydrocarbon to produce a trialkyl gallium.

Starting Materials

<Gallium>

Gallium is as described above in connection with method 1.

<Magnesium>

Magnesium is as described above in connection with the first aspect of method 2.

<Solvents>

Usable hydrocarbons are not limited and examples include pentane, hexane, heptane, octane, nonane, decane, undecane, dodecane, and like saturated aliphatic hydrocarbons; cyclohexane, cycloheptane, and like saturated alicyclic hydrocarbons; toluene, xylene, trimethylbenzene, ethylbenzene, ethyltoluene, indene, and like aromatic hydrocarbons; etc.

Preferable hydrocarbons are those that are easily separable from the resulting trialkyl gallium. In general, preferable hydrocarbons are usually those that have boiling points greatly different from that of the trialkyl gallium. However, use of a hydrocarbon that has a lower boiling point than the trialkyl gallium, even if they have sufficiently different boiling points, results in yield compromise due to a small amount of azeotropic mixture. Therefore, it is advantageous to select a hydrocarbon having a higher boiling point than the trialkyl gallium. However, since the handling of hydrocarbons that are solid at ordinary temperatures requires more labor, it is advantageous to select hydrocarbons that have lower boiling points than such hydrocarbons.

Hydrocarbons may be used singly or as a combination of two or more kinds. For ease of purifying the resulting trialkyl gallium, it is preferable to use a single hydrocarbon.

<Alkyl Halides>

Usable alkyl iodides and alkyl bromides are usually those that have a $C_{1-10}$ alkyl group, and preferably a $C_{1-4}$ alkyl group. Alkyl iodides and alkyl bromides having an alkyl group with an aforementioned number of carbon atom(s) are highly reactive. The use of such an alkyl halide enables the production of a trialkyl gallium that is sufficiently volatile for an MOCVD ingredient.

Alkyl iodides and alkyl bromides may be used singly or as a combination of two or more kinds. When two or more kinds of such alkyl halides are used in combination, such alkyl halides having different kinds of halogen atom or having different kinds of alkyl group may be used.

Specific examples of alkyl iodides having a $C_{1-4}$ alkyl group are methyl iodide, ethyl iodide, n-propyl iodide, isopropyl iodide, n-butyl iodide, isobutyl iodide, sec-butyl iodide, and tert-butyl iodide. Specific examples of alkyl bromides having a $C_{1-4}$ alkyl group are methyl bromide, ethyl bromide, n-propyl bromide, isopropyl bromide, n-butyl bromide, isobutyl bromide, sec-butyl bromide, and tert-butyl bromide. Among these examples, methyl iodide, ethyl iodide, n-propyl iodide, isopropyl iodide, methyl bromide, ethyl bromide, n-propyl bromide, and isopropyl bromide are preferable, with methyl iodide, ethyl iodide, and n-propyl iodide being particularly preferable.

Proportions

It is presumed that the reaction that produces trialkyl gallium, i.e., the reaction of gallium, magnesium and alkyl halide, follows Reaction Formula (2) above. The molar ratio of magnesium to gallium is preferably about 1 to about 20 mol of magnesium per mol of gallium, more preferably about 2 to about 10 mol, and particularly preferably about 1 to about 3 mol. With a molar ratio being within such a range, the reaction of gallium, magnesium, and an alkyl halide can efficiently proceed to a practically sufficient extent, and a trialkyl gallium can be produced in an enhanced yield.

Stoichiometrically, by reference to Reaction Formula (2), $(a+3)/2$ mol of alkyl halide(s) selected from the group consisting of alkyl iodides and alkyl bromides is necessary per mol of gallium and $a/2$ mol of magnesium to produce a trialkyl gallium, and the amount of alkyl halide thus varies according to the amount of gallium and the molar ratio of gallium to magnesium. The amount of alkyl halide(s) selected from alkyl iodides and alkyl bromides is usually about 50 to about 200% of $(a+3)/2$ mol, and preferably about 70 to about 150% of $(a+3)/2$ mol. With an amount being within such a range, a trialkyl gallium can be obtained in an enhanced yield.

First Process (Preactivation Process)

In the second aspect of method 2, gallium and magnesium are subjected to preactivation prior to the reaction with alkyl halide(s) selected from the group consisting of alkyl iodides and alkyl bromides. That is, a mixture of magnesium and molten gallium is heated in a vacuum. This preactivation contributes not only to the removal of moisture present on the surface of the gallium and magnesium and to the production of an alkyl magnesium halide but also to uniform mixing of the gallium and magnesium. This preactivation is as described in connection with the first aspect of method 2.

Second Step (Synthesizing Reaction Process)

In the second aspect of method 2, the synthesizing reaction is carried out in an aforementioned inert gas atmosphere.

The reaction is carried out by introducing a mixture of activated gallium and magnesium, a hydrocarbon, and alkyl halide(s) selected from the group consisting of alkyl iodides and alkyl bromides into a reaction vessel filled with an inert gas. In particular, for ease of introduction into the reaction vessel, it is advantageous to introduce into the reaction vessel in the order of gallium-magnesium mixture and hydrocarbon, and then slowly alkyl halide(s) selected from the group consisting of alkyl iodides and alkyl bromides.

The amount of hydrocarbon is not limited. It is preferably such that the gallium content and the magnesium content in the solvent at the beginning of the reaction (the gallium content and the magnesium content independently refer to molar amounts per liter of solvent) are both independently about 0.01 to about 10 mol/l, and more preferably about 0.1 to about 5 mol/l. With contents being within such a range, the reactivity of the ingredients can be sufficiently enhanced, resulting in an enhanced trialkyl gallium yield, while the reaction can be easily controlled. That is, sudden and excessive advancement of the reaction, untimely termination of the reaction due to precipitation of alkyl magnesium halide, and difficulty of stirring due to by-product magnesium halide do not occur.

The reaction temperature is suitably selected to efficiently carry out the reaction in consideration of the type of hydrocarbon and alkyl halide used and other factors. When a gallium-magnesium mixture, hydrocarbon, and alkyl halide are mixed, the temperature of the reaction solution increases. After mixing the compounds, especially after introducing all of the alkyl halide, the reaction is carried out while controlling the temperature of the reaction solution usually within about 0 to about 200° C., preferably about 40 to about 160° C., and more preferably about 60 to about 120° C. Usually, 3 to 30 hours of reaction produces a trialkyl gallium.

Furthermore, the synthesizing reaction pressure is not limited, and the reaction can be carried out under atmospheric pressure, under reduced pressure, or under increased pressure.

Purification Process

The purification process is as described in connection with method 1.

(3) Third Aspect

The third aspect of method 2 is described below in detail. A method for producing a trialkyl gallium encompassed within the third aspect of method 2 comprises a first step of heating in a vacuum a mixture of magnesium and molten gallium and a second step of reacting the vacuum-heated mixture with at least one alkyl chloride in at least one hydrocarbon to produce a trialkyl gallium.

Starting Materials

<Gallium>

Gallium is as described above in connection with method 1.

<Magnesium>

Magnesium is as described above in connection with the first aspect of method 2.

<Solvents>

Usable hydrocarbons are as described in connection with the second aspect of method 2.

<Alkyl Chlorides>

Alkyl chlorides are as described in connection with the first aspect of method 2.

Proportions

The proportions of gallium, magnesium and alkyl chloride are as described in connection with the first aspect of method 2.

First Process (Preactivation Process)

In the third aspect of method 2, gallium and magnesium are subjected to preactivation prior to the reaction with an alkyl chloride. That is, a mixture of magnesium and molten gallium is heated in a vacuum. This preactivation contributes not only to the removal of moisture present on the surface of the gallium and magnesium and to the production of an alkyl magnesium chloride but also to uniform mixing of the gallium and magnesium. In particular, the reactivity of an alkyl chloride to gallium is weaker than to magnesium so that this preactivation is considered effective with magnesium as well as gallium. This preactivation is as described in connection with the first aspect of method 2.

Second Step (Synthesizing Reaction Process)

In the third aspect, the synthesizing reaction is carried out in an aforementioned inert gas atmosphere. Moisture and oxygen present in a gas atmosphere should be removed as described above.

The reaction is carried out by introducing an activated gallium-magnesium mixture, a hydrocarbon, and alkyl chloride(s) into a reaction vessel filled with an inert gas. In particular, for ease of introduction into the reaction vessel, it is advantageous to introduce into the reaction vessel in the order of a gallium-magnesium mixture and a hydrocarbon, and then slowly alkyl chloride(s).

The amount of hydrocarbon is not limited. It is preferably such that the gallium content and the magnesium content in the solvent at the beginning of the reaction (the gallium content and the magnesium content independently refer to molar amounts per liter of solvent) are both independently about 0.01 to about 10 mol/l, and more preferably about 0.1 to about 5 mol/l. With contents being within such a range, the reactivity of the ingredients can be sufficiently enhanced, resulting in an enhanced trialkyl gallium yield, while the reaction can be easily controlled. That is, sudden and excessive advancement of the reaction, untimely termination of the reaction due to precipitation of alkyl magnesium chloride, and difficulty of stirring due to by-product magnesium chloride do not occur.

The reaction temperature is suitably selected to efficiently carry out the reaction in consideration of the type of hydrocarbon and alkyl chloride used and other factors. When a gallium-magnesium mixture, hydrocarbon, and alkyl chloride are mixed, the temperature of the reaction solution increases. After mixing the compounds, especially after introducing all of the alkyl chloride, the reaction is carried out while controlling the temperature of the reaction solution usually within about 0 to about 200° C., preferably about 40 to about 160° C., and more preferably about 60 to about 120° C. Usually, 3 to 30 hours of reaction produces a trialkyl gallium.

Furthermore, the synthesizing reaction pressure is not limited, and the reaction can be carried out under atmospheric pressure, under reduced pressure, or under increased pressure.

Purification Process

The purification process is as described in connection with method 1.

(III) Method 3

Method 3 of the present invention is described below in detail. A method for producing a trialkyl gallium encompassed within method 3 of the present invention comprises a step of reacting at least one alkylgallium halide represented by General Formula (3) above with at least one alkyl metal.

Starting Materials

<Gallium Compounds>

The type of halogen atom contained in alkylgallium halides represented by General Formula (3) is not limited, and is usually selected from chlorine, bromine, and iodine. Among alkylgallium halides, alkylgallium iodides and alkylgallium bromides are preferable for their high reactivity, with alkylgallium iodides being particularly preferable.

In General Formula (3), R is preferably a methyl group since great demand exists for trimethyl gallium as an MOCVD ingredient.

Specific examples of compounds represented by General Formula (3) are $Ga_2MeCl_5$, $Ga_2Me_2Cl_4$, $Ga_2Me_3Cl_3$, $Ga_2Me_4Cl_2$, $Ga_2Me_5Cl$, $Ga_2MeBr_5$, $Ga_2Me_2Br_4$, $Ga_2Me_3Br_3$, $Ga_2Me_4Br_2$, $Ga_2Me_5Br$, $Ga_2MeI_5$, $Ga_2Me_2I_4$, $Ga_2Me_3I_3$, $Ga_2Me_4I_2$, $Ga_2Me_5I$, $Ga_2EtCl_5$, $Ga_2Et_2Cl_4$, $Ga_2Et_3Cl_3$, $Ga_2Et_4Cl_2$, $Ga_2Et_5Cl$, $Ga_2EtBr_5$, $Ga_2Et_2Br_4$, $Ga_2Et_3Br_3$, $Ga_2Et_4Br_2$, $Ga_2Et_5Br$, $Ga_2EtI_5$, $Ga_2Et_2I_4$, $Ga_2Et_3I_3$, $Ga_2Et_4I_2$, and $Ga_2Et_5I$. Among these examples, $Ga_2Me_2Br_4$, $Ga_2Me_3Br_3$, $Ga_2Me_4Br_2$, $Ga_2Me_5Br$, $Ga_2Me_2I_4$, $Ga_2Me_3I_3$, $Ga_2Me_4I_2$, $Ga_2Me_5I$, $Ga_2Et_2Br_4$, $Ga_2Et_3Br_3$, $Ga_2Et_4Br_2$, $Ga_2Et_5Br$, $Ga_2Et_2I_4$, $Ga_2Et_3I_3$, $Ga_2Et_4I_2$, and $Ga_2Et_5I$ are preferable. $Ga_2Me_2I_4$, $Ga_2Me_3I_3$, $Ga_2Me_4I_2$, and $Ga_2Me_5I$ are particularly preferable.

Alkylgallium halide compounds represented by General Formula (3) may be used singly or as a combination of two or more kinds.

Compounds represented by General Formula (3) can be produced according to prior-art methods in which gallium and alkyl halides are reacted. For example, $Ga_2R_3X_3$ can be produced according to a method described in M. J. S. Gynane, I. J. Worrall, *J. Organomet. Chem.*, 40, C59 (1972). $Ga_2R_2I_4$ can be produced according to a method described in M. Wilkinson, I. J. Worrall, *J. Organomet. Chem.*, 93, 39 (1975). $Ga_2RBr_5$ can be produced according to methods described in W. Lind, I. J. Worrall, *J. Organomet. Chem.*, 36, 35 (1972), and *J. Organomet. Chem.*, 40, 35 (1972). A person skilled in the art can produce other alkylgallium halides represented by General Formula (3) with reference to these publications. In addition, compounds of General Formula (3) can be produced according to prior-art methods in which gallium halides and alkyl metals are reacted.

The electrical properties and optical properties of a compound semiconductor produced by MOCVD depends greatly on the purity of the starting organometallic compound. Therefore, a trialkyl gallium of high purity should be produced. Since the purity of the resulting trialkyl gallium depends on the purity of the starting compound, the compound of General Formula (3) should be of high purity.

A compound of General Formula (3) may be prepared using high-purity gallium or a high-purity gallium halide as a starting material. Such gallium and gallium halide may be commercial products with a purity of 99.9% (3N) to 99.99999% (7N). While gallium/gallium halide having a purity exceeding 4N is commercially available, such gallium/gallium halide can be also obtained by purifying a commercially available product having a purity of 3N or 4N by, e.g., recrystallization, reduced pressure purification, electrolytic refining, etc. The purity of the starting gallium/gallium halide is preferably 99.999% (5N) or better, and more preferably 99.9999% (6N) or better.

<Alkyl Metals>

Alkyl metals refer to compounds having a bond between an alkyl group and a metal. The type of alkyl metal is not limited. In particular, alkyl lithiums, alkyl magnesiums, alkyl aluminums, and alkyl zincs are preferable. The alkyl group is usually a methyl or ethyl group. The alkyl group is preferably a methyl group since great demand exists for trimethyl gallium as an MOCVD ingredient.

Examples of alkyl metals are alkyl magnesium halides (Grignard reagents), alkyl lithiums, trialkyl aluminums, dialkyl zincs, and the like containing a methyl or ethyl group as an alkyl group. In particular, alkyl magnesium halides and trialkyl aluminums are preferable for not posing a safety concern during trialkyl gallium production and for allowing the resulting trialkyl gallium to be easily purified.

Specific examples of alkyl magnesium halides (Grignard reagents) are methyl magnesium chloride, ethyl magnesium chloride, methyl magnesium bromide, ethyl magnesium bromide, methyl magnesium iodide, and ethyl magnesium iodide. In particular, methyl magnesium iodide and ethyl magnesium iodide are preferable due to their high reactivity.

Specific examples of alkyl lithiums include methyl lithium and ethyl lithium. Specific examples of trialkyl aluminums include trimethyl aluminum and triethyl aluminum. Specific examples of dialkyl zincs include dimethyl zinc and diethyl zinc.

Methods for producing alkyl magnesium halides are known. An alkyl magnesium halide can be produced by reacting magnesium and an alkyl halide in an ether or a like solvent. Alkyl magnesium halides (Grignard reagents) having a methyl or ethyl group as an alkyl group are commercially available.

Methods for producing alkyl lithiums are known. An alkyl lithium compound can be produced by, for example, reacting metallic lithium with an alkyl chloride or alkyl bromide in an ether. Methyl lithium and ethyl lithium are commercially available.

Methods for producing trialkyl aluminums are known. For example, a trialkyl aluminum can be produced according to the method described in S. G. Wilkinson, F. G. A. Stones, E. W. Abel, *Comprehensive Organometallic Chemistry*, The Synthesis, Reactions and Structures of Organometallic Compounds Vol. 1, Pergamon Press Ltd., (1982), Chapter 6. Trimethyl aluminum and triethyl aluminum are commercially available.

Methods for producing dialkyl zincs are known. For example, a dialkyl zinc can be produced by reacting an alkyl iodide and metallic zinc in an ether or hydrocarbon solvent. Dimethyl zinc and diethyl zinc are commercially available.

Regarding the purity of alkyl metals, commercially available trialkyl aluminums and dialkyl zincs having a purity of 5N or 6N for use in electronic materials are usable as received. In addition, commercially available products of standard grade having a purity of 2N can be purified by distillation for use. Since there are no commercially available alkyl magnesium halides and alkyl lithiums of high purity, alkyl magnesium halides and alkyl lithiums of high purity may be produced using magnesium or lithium having a purity of at least 3N as starting materials. Although magnesium and lithium having a purity of at least 3N are commercially available, the higher the purity, the more expensive they are. Therefore, usable alkyl magnesium halides and alkyl lithiums may be produced using commercially available products having a purity of 2N to 4N by subjecting them to purification by vacuum distillation, vacuum sublimation, etc.

Alkyl metals may be used singly or as a combination of two or more compounds of the same type. For example, two or more alkyl lithiums can be used in combination, but an alkyl lithium and trialkyl aluminum are barely usable together.

<Solvents>

The synthesizing reaction of method 3 of the present invention is usually carried out in a solvent although it can be carried out in the absence of a solvent when the alkyl metal is liquid. Commercially available alkyl magnesium halides (Grignard reagents) and alkyl lithiums are usually sold dissolved in a solvent, i.e., a solution form, and therefore when such alkyl metals are used, another solvent need not be used.

Solvents are not limited insofar as they do not contain active hydrogen which reacts with the resulting trialkyl gallium, such as alcoholic and thiol compounds do. Examples of usable solvents are ethers, hydrocarbons, amines, and like known solvents. In particular, ethers and amines are preferable for enhancing reactivity in producing trialkyl galliums.

Examples of hydrocarbons are pentane, hexane, heptane, octane, nonane, decane, undecane, dodecane, and like saturated aliphatic hydrocarbons; cyclohexane, cycloheptane, and like saturated alicyclic hydrocarbons; toluene, xylene, trimethylbenzene, ethylbenzene, ethyltoluene, indene, and like aromatic hydrocarbons; etc.

Preferable hydrocarbons are those that are easily separable from the resulting trialkyl gallium. In general, preferable hydrocarbons are usually those that have boiling points greatly different from that of the trialkyl gallium. However, use of a hydrocarbon that has a lower boiling point than the trialkyl gallium, even if they have sufficiently different boiling points, results in yield compromise due to a small amount of azeotropic mixture. Therefore, it is advantageous to select a hydrocarbon having a higher boiling point than the trialkyl gallium. However, since the handling of hydrocarbons that are solid at ordinary temperatures requires more labor, it is advantageous to select hydrocarbons that have lower boiling points than such hydrocarbons.

Examples of ethers are diethyl ether, di-n-propyl ether, diisopropyl ether, di-n-butyl ether, diisobutyl ether, di-sec-butyl ether, diisopentyl ether (diisoamyl ether), and like aliphatic ethers; anisole, methylanisole, benzyl methyl ether, ethylanisole, dimethylanisole, isopropylanisole, phenetole, and like aromatic ethers; etc.

Ethers form an adduct with the resulting trialkyl gallium. Therefore, it is preferable to isolate the trialkyl gallium by distillation to thermally decompose the ether adduct, as described below. In this connection, the ether used preferably has a higher boiling point than the trialkyl gallium. Moreover, when the thermal decomposition temperature of a trialkyl gallium ether adduct is higher than that of the trialkyl gallium, the thermal decomposition of the ether adduct is accompanied by decomposition of the trialkyl gallium. Therefore, it is preferable to select an ether such that the thermal decomposition temperature of the ether adduct is lower than that of the resulting trialkyl gallium.

Examples of usable amines include tertiary amines. Specific examples are trimethylamine, triethylamine, tri-n-propyl amine, triisopropylamine, tri-n-butylamine, triisobutylamine, tri-sec-butylamine, tri-tert-butylamine, and like aliphatic tertiary amines; and pyridine, pyrrole, pyrimidine, pyrazine, pyridazine, 1,3,5-triazine, hexahydrotriazine, and like heterocyclic tertiary amines.

Amines form an adduct with the resulting trialkyl gallium. Therefore, it is preferable to isolate the trialkyl gallium by distillation to thermally decompose the amine adduct, as described below. Therefore, when the thermal decomposition temperature of a trialkyl gallium amine adduct is higher than that of the trialkyl gallium, the thermal decomposition of the amine adduct is accompanied by decomposition of the trialkyl gallium. Therefore, it is advantageous to select an amine such that the thermal decomposition temperature of its adduct is lower than that of the product trialkyl gallium.

Solvents may be used singly or as a combination of two or more kinds. For ease of purifying the resulting trialkyl gallium, it is advantageous to use a single solvent.

Proportions

The proportions of alkyl gallium halide represented by General Formula (3) and alkyl metal vary according to the type of alkyl metal.

When the alkyl metal is an alkyl magnesium halide, the reaction for producing a trialkyl gallium can be expressed as Reaction Formula (5):

$$Ga_2R_mX_{6-m}+(6-m)RMgX \rightarrow 2GaR_3+(6-m)MgX_2 \qquad (5)$$

With reference to Reaction Formula (5), stoichiometrically, 6−m mol of alkyl magnesium halide is used per mol of alkylgallium halide represented by General Formula (3). It may be preferable to use about 0.5(6−m) to about 2(6−m) mol of alkyl magnesium halide per mol of compound of General Formula (3), and more preferably about 0.7(6−m) to about 1.5(6−m) mol.

When the alkyl metal is an alkyl lithium, the reaction for producing a trialkyl gallium can be expressed as Reaction Formula (6):

$$Ga_2R_mX_{6-m}+(6-m)RLi \rightarrow 2GaR_3+(6-m)LiX \qquad (6)$$

With reference to Reaction Formula (6), stoichiometrically, 6−m mol of alkyl lithium is used per mol of alkylgallium halide represented by General Formula (3). It may be preferable to use about 0.5(6−m) to about 2(6−m) mol of alkyl lithium per mol of compound of General Formula (3), and more preferably about 0.7(6−m) to about 1.5(6−m) mol.

When the alkyl metal is a trialkyl aluminum, the reaction for producing a trialkyl gallium can be expressed as Reaction Formula (7):

$$Ga_2R_mX_{6-m}+(6-m)/3 AlR_3 \rightarrow 2GaR_3+(6-m)/3 AlX_3 \qquad (7)$$

With reference to Reaction Formula (7), stoichiometrically, (6−m)/3 mol of trialkyl aluminum is used per mol of alkylgallium halide represented by General Formula (3). It may be preferable to use about 0.5[(6−m)/3] to about 2[(6−m)/3] mol of trialkyl aluminum per mol of compound of General Formula (3), and more preferably about 0.7[(6−m)/3] to about 1.5[(6−m)/3] mol.

When the alkyl metal is a dialkyl zinc, the reaction for producing a trialkyl gallium can be expressed as Reaction Formula (8):

$$Ga_2R_mX_{6-m}+(6-m)/2 ZnR_2 \rightarrow 2GaR_3+(6-m)/2 ZnX_2 \qquad (8)$$

With reference to Reaction Formula (8), stoichiometrically, (6−m)/2 mol of dialkyl zinc is used per mol of alkylgallium halide represented by General Formula (3). It may be preferable to use about 0.5[(6−m)/2] to about 2[(6−m)/2] mol of dialkyl zinc per mol of compound of General Formula (3), and preferably about 0.7[(6−m)/2] to about 1.5[(6−m)/2] mol.

When any such alkyl metal is used, if the proportion is within an aforementioned, the reaction progresses sufficiently. Use of an alkyl metal in excessively high proportions does not bring about any extra effect, and increases the amount of material to be disposed of, thereby making the work-up laborsome and increasing the production costs. Such problems do not occur when the proportions are within an aforementioned range.

Synthesizing Reaction Process

The synthesizing reaction of method 3 of the present invention is carried out in an inert gas atmosphere such as nitrogen, helium, neon, argon, krypton, xenon, etc. The production of the alkylgallium halide compound and alkyl metal is also carried out in an inert gas atmosphere. The purity of the inert gas is preferably 99.99% (4N) or better, and particularly preferably 99.9999% (6N) or better.

It is desirable to use an atmosphere gas from which moisture and oxygen have been removed as much as possible because moisture and oxygen present in an atmosphere gas result in not only an impaired trialkyl gallium yield but also in purity compromise. The atmosphere gas preferably has a dew point of −80° C. or lower and an oxygen content of 100 ppb or less, and particularly preferably a dew point of −100° C. or lower and an oxygen content of 10 ppb or less. Such a highly pure inert gas can be obtained by membrane separation, catalytic reaction, fluid rectification, PSA (pressure swing adsorption), etc.

The reaction is carried out by contacting an alkylgallium halide of General Formula (3) with an alkyl metal, typically in a solvent in an inert gas atmosphere. The order of introduction of these compounds into the reaction vessel is not limited. It is usually advantageous to introduce in the order of solvent and alkylgallium halide, and then alkyl metal. When the reactivity between the alkylgallium halide and alkyl metal is high, the alkyl metal is introduced little by little. When the reactivity is low, the alkyl metal may be introduced at once.

The amount of solvent is not limited. It is preferably such that the alkylgallium halide content and alkyl metal content in the solvent right after the introduction of the alkyl metal (the alkylgallium halide content and the alkyl metal content independently refer to molar amounts per liter of solvent) are both independently about 0.01 to about 10 mol/l, and more preferably about 0.1 to about 5 mol/l. With contents being within such a range, the reactivity of the ingredients can be sufficiently enhanced, resulting in an enhanced trialkyl gallium yield, while the reaction can be easily controlled. That is, sudden and excessive advancement of the reaction, untimely termination of the reaction due to precipitation of alkyl magnesium halide, and difficulty of stirring due to by-product magnesium halide do not occur.

The reaction temperature is suitably selected to efficiently carry out the reaction in consideration of the type of alkylgallium halide, alkyl metal and solvent used, and other factors. The reaction is usually carried out at about 0 to about 200° C., preferably about 40 to about 160° C., and more preferably about 60 to about 120° C. Usually, 3 to 30 hours of reaction within such a temperature range produces a trialkyl gallium.

Furthermore, the reaction pressure is not limited, and the reaction can be carried out under atmospheric pressure, under reduced pressure, or under increased pressure.

Purification Process

The purification process is as described in connection with method 1.

(IV) Gallium-Based Compound Semiconductor Device

A gallium-based compound semiconductor thin film for a gallium-based compound semiconductor device can be created by, for example, epitaxial growth by MOCVD using as starting materials a trialkyl gallium produced according to any one of methods 1 to 3 of the present invention in combination with at least one group VB (group 15) element-containing compound selected from the group consisting of nitrogen-containing compounds, phosphorus-containing compounds, and arsenic-containing compounds. A typical example of a gallium-based compound semiconductor thin film is a gallium nitride-based compound semiconductor thin film created using a trialkyl gallium and a nitrogen-containing compound such as ammonia.

Such a semiconductor may have a homo, hetero or double hetero structure with an MIS (metal insulator semiconductor) junction, PIN junction, pn junction or the like. Emission wavelengths can be selected depending on the materials of the semiconductor layer and the extent of mixed crystal formation. Moreover, such a semiconductor may have a single quantum well or multi-quantum well structure in which a semiconductive active layer is formed as a thin film that gives a quantum effect.

In the exampled gallium nitride-based compound semiconductor thin film, sapphire, spinel, SiC, Si, ZnO, GaN, and like materials are preferably usable as the substrates of such gallium nitride-based compound semiconductors. It is advantageous to use a sapphire substrate to produce highly crystalline nitride semiconductors with high mass-producibility. A gallium nitride-based compound semiconductor may be created on such a sapphire substrate by MOCVD or like method. A buffer layer composed of GaN, AlN, GaAlN, or the like is formed on the sapphire substrate, and a nitride semiconductor having a pn junction is formed thereon.

Examples of pn junction-equipped light-emitting devices using a gallium nitride-based compound semiconductor include those that have a double hetero structure in which a first contact layer composed of n-type GaN, a first cladding layer composed of n-type GaAlN, an active layer composed of InGaN, a second cladding layer composed of p-type GaAlN, and a second contact layer composed of p-type GaN are layered on a buffer layer in this order, and like light-emitting devices.

Gallium nitride-based compound semiconductors show n-type conductivity when not doped with impurities. It is advantageous to suitably use Si, Ge, Se, Te, C, and like n-type dopants when forming n-type nitride semiconductors with enhanced emission efficiency. In contrast, when p-type gallium nitride-based compound semiconductors are formed, p-type dopants such as Zn, Mg, Be, Ca, Sr, Ba, and the like are used. Gallium nitride-based compound semiconductors are not likely to be p-typed just by introducing a p-type dopant, and therefore, after the introduction of a p-type dopant, it is preferable to reduce the resistance by furnace heating, plasma irradiation, etc. After electrode formation, a light-emitting device composed of a nitride semiconductor can be obtained by cutting it in the form of a chip from a semiconductor wafer.

EXAMPLES

Examples are given below to illustrate the present invention in more detail, but the scope of the invention is not limited to these examples.

Examples 1-1 to 1-3 are encompassed within method 1 of the present invention, and Comparative Examples 1-1 to 1-3 are presented for comparison.

Example 1-1

Production of Trimethyl Gallium 10.00 g (143 mmol) of gallium, 9.53 g (392 mmol) of magnesium in the form of shavings, and 52 ml of diisoamyl ether that has been fully dehydrated with molecular sieves are introduced into a nitrogen-purged, 300-ml four-neck flask at room temperature such that the magnesium content in the slurry is 7.54 mol/l.

The gallium has a purity of 6N, and the magnesium has a purity of 3N. The nitrogen has a purity of 6N, a dewpoint of −110° C., and an oxygen content of 1 ppb.

After the flask is equipped with a dry-ice condenser and the inner temperature is adjusted to 20° C., 101.5 g (715 mmol) of separately weighed methyl iodide is added dropwise to the solution in the flask while stirring the solution over a period of about 1 hour. During the dropwise addition of methyl iodide, crystals of magnesium iodide are precipitated, followed by the precipitation of supersaturated methyl magnesium iodide. As the precipitation of methyl magnesium iodide proceeds, the temperature increase of the flask ceases. 104 ml of diisoamyl ether that has been fully dehydrated with molecular sieves is then added to the flask. The total amount of diisoamyl ether added to the reaction system is 156 ml, and the slurry is thus diluted to a magnesium content of 2.51 mol/l.

Methyl magnesium iodide that has reached supersaturation dissolves again, and the temperature of the slurry in the flask increases due to the addition of methyl iodide. All of the methyl iodide is added, and the mixture is stirred for 18 hours while maintaining the temperature of the flask at 110° C.

After the reaction, a large amount of white magnesium iodide is precipitated. While evaporating off diisoamyl ether, crude trimethyl gallium is isolated by fractional distillation from the reaction mixture using a glass bead-packed column having a length of 30 cm and a diameter of 1.5 cm.

A quantitative determination of gallium by inductively coupled plasma atomic emission spectrometry (ICP-AES) shows that 13.8 g of crude trimethyl gallium is obtained (yield: 84.0% calculated as the equivalent amount of gallium).

Example 1-2

Production of Trimethyl Gallium 10.00 g (143 mmol) of gallium, 9.41 g (387 mmol) of magnesium in the form of shavings, and 50 ml of diisoamyl ether that has been fully dehydrated with molecular sieves are introduced into a nitrogen-purged, 300-ml glass autoclave such that the magnesium content in the slurry is 7.74 mol/l.

The gallium has a purity of 6N, and the magnesium has a purity of 3N. The nitrogen has a purity of 6N, a dewpoint of −110° C., and an oxygen content of 1 ppb.

After the flask is equipped with a dry ice condenser and the inner temperature of the flask is adjusted to 20° C., 67.4 g (710 mmol) of separately weighed methyl bromide is bubbled through the solution in the flask while stirring the solution over a period of about 2 hours. During the course of bubbling of the methyl bromide, crystals of magnesium bromide are precipitated, followed by the precipitation of supersaturated methyl magnesium bromide. As the precipitation of methyl magnesium bromide proceeds, the temperature increase of the flask ceases. 100 ml of diisoamyl ether that has been fully dehydrated with molecular sieves is then added to the flask. The total amount of diisoamyl ether added to the reaction system is 150 ml, and the slurry is thus diluted to a magnesium content of 2.58 mol/l.

Methyl magnesium bromide that has reached supersaturation dissolves again, and the inner temperature of the flask increases again due to the addition of methyl bromide. When all of the methyl bromide is bubbled and the refluxing of methyl bromide is terminated, the solution is stirred for 18 hours while maintaining the inner temperature of the autoclave at 110° C.

After the reaction, a large amount of white magnesium bromide is precipitated. While evaporating off diisoamyl ether, crude trimethyl gallium is isolated by fractional distillation from the reaction mixture using a glass bead-packed column having a length of 30 cm and a diameter of 1.5 cm.

A quantitative determination of gallium by ICP-AES shows that 10.2 g of crude trimethyl gallium is obtained (yield: 62.0% calculated as the equivalent amount of gallium).

Comparative Example 1-1

Production of Trimethyl Gallium (without Isoamyl Ether Dilution)

Trimethyl gallium is produced in a similar manner as in Example 1-1, except that the amount of diisoamyl ether added before the reaction is 156 ml, and no diisoamyl ether is added during the reaction.

A quantitative determination of gallium by ICP-AES showed that 3.3 g of crude trimethyl gallium is obtained by fractional distillation (yield: 19.8% calculated as the equivalent amount of gallium).

Comparative Example 1-2

Production of Trimethyl Gallium (with Magnesium Powders)

Trimethyl gallium is produced in a similar manner as in Example 1-1, except that 9.41 g of magnesium powders (387 mmol) having a mean particle diameter of 45 μm (measured by a Mastersizer 2000 manufactured by Malvern Instruments Ltd. is used in place of 9.41 g of magnesium shavings (387 mmol), the amount of diisoamyl ether added before the reaction is 156 ml, and no diisoamyl ether is added during the reaction.

A quantitative determination of gallium by ICP-AES shows that 13.5 g of crude trimethyl gallium is obtained by fractional distillation (yield: 82.0% calculated as the equivalent amount of gallium).

Comparative Example 1-3

Production of Trimethyl Gallium (with a Gallium-Magnesium Alloy)

Trimethyl gallium is produced in a similar manner as in Example 1-1, except that 20.5 g of a gallium-magnesium alloy (molar ratio: gallium/magnesium=2/5) is used in place of a mixture of gallium and magnesium shavings; the amount of diisoamyl ether added before the reaction is 156 ml; and no diisoamyl ether is added during the reaction.

A quantitative determination of gallium by ICP-AES shows that 14.5 g of crude trimethyl gallium is obtained by fractional distillation (yield: 84.0% calculated as the equivalent amount of gallium).

The results of the examples presented above show that the method of Comparative Example 1-1 in which the magnesium content is not reduced during the reaction results in a very low yield, and is not at all practical. The method of Comparative Example 1-2 provides a high yield even though magnesium is not diluted during the reaction; however, the method involves the use of magnesium powder which is difficult to handle. The method of Comparative Example 1-3 provides a high yield using a gallium-magnesium alloy, but requires alloy production which is very difficult. Moreover, the yield of trimethyl gallium is not consistent when an alloy is used.

In contrast, the methods of Examples 1-1 and 1-2 according to the present invention do not involve the preparation of a gallium-magnesium alloy, and allow trimethyl gallium to be produced in high yields using magnesium shavings which are easy to handle.

Example 1-3

Production of a Gallium Nitride-Based Compound Semiconductor Device

A sapphire (C plane) substrate is placed in a reaction vessel for metalorganic vapor phase epitaxy (MOVPE), and is cleaned in a stream of hydrogen with the substrate temperature being 1050° C.

(Buffer Layer)

The substrate temperature is then decreased to 510° C., and a GaN buffer layer having a thickness of about 150 Å is grown on the substrate using hydrogen as a carrier gas, and trimethyl gallium produced by purifying crude trimethyl gallium of Example 1-1 and ammonia as source gases. This reaction is represented by the following formula:

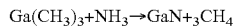

(Undoped GaN Layer)

After the growth of the buffer layer, the supply of trimethyl gallium only is stopped, and then the substrate temperature is increased to 1050° C. At 1050° C., an undoped GaN layer having a thickness of 1.5 μm is grown similarly using trimethyl gallium and ammonia as source gases.

(N-Side Contact Layer)

With the temperature being maintained at 1050° C., an n-side contact layer of $4.5 \times 10^{18}/cm^3$ Si-doped GaN is subsequently grown to a thickness of 2.25 μm using trimethyl gallium and ammonia as source gases and silane as a dopant gas.

(First n-Side Multilayer)

The supply of the silane only is stopped, and then a 75-Å thick undoped GaN layer is grown at 1050° C. using trimethyl gallium and ammonia. With the temperature being maintained at 1050° C., a 25-Å thick, $4.5 \times 10^{18}/cm^3$ Si-doped GaN layer is subsequently grown by supplying silane. This resulted in the formation of a pair of layers A and B, i.e., a 75-Å thick undoped GaN layer and a 25-Å thick Si-doped GaN layer, respectively. In this manner, twenty-five such pairs are deposited to form a lamination having a thickness of 2500 Å, thereby giving a first n-side multilayer composed of multilayered films having a superlattice structure.

(Second n-Side Multilayer)

A nitride semiconductor layer 1 composed of undoped GaN is grown to a thickness of 40 Å at 1050° C. The temperature is then decreased to 800° C., and on the nitride semiconductor layer 1, a nitride semiconductor layer 2 composed of undoped $In_{0.13}Ga_{0.87}N$ is grown to a thickness of 20 Å using trimethyl gallium, trimethylindium, and ammonia. This procedure is repeated to form a lamination of ten pairs of alternating layers 1 and 2 in order. Lastly, a 40-Å thick, a nitride semiconductor layer 1 composed of GaN is grown on top of the lamination, resulting in a 640-Å thick, second n-side multilayer composed of multilayered films having a lattice structure.

(Active Layer)

An undoped-GaN barrier layer is grown to a thickness of 200 Å, and at 800° C., an undoped-$In_{0.4}Ga_{0.6}N$ well layer is then grown to a thickness of 30 Å using trimethyl gallium, trimethylindium, and ammonia. Five barrier layers and four well layers are alternately formed on top of one another in the order of a barrier layer, well layer, barrier layer, well layer, . . . , and barrier layer, thereby giving an active layer with a multiple-quantum well structure having a total thickness of 1120 Å.

(P-Side Multilayered Cladding Layer)

Next, a nitride semiconductor layer 3 of p-type $Al_{0.2}Ga_{0.8}N$ doped with $1 \times 10^{20}/cm^3$ Mg is grown at 1050° C. to a thickness of 40 Å using trimethyl gallium, trimethyl aluminum, ammonia, and biscyclopentadienyl magnesium. After the temperature is decreased to 800° C., a nitride semiconductor layer 4 of $In_{0.03}Ga_{0.97}N$ doped with $1 \times 10^{20}/cm^3$ Mg is grown to a thickness of 25 Å using trimethyl gallium, trimethylindium, ammonia, and biscyclopentadienylmagnesium. This procedure is repeated to form a lamination of five pairs of alternating layers 3 and 4 in order. Lastly, a nitride semiconductor layer 3 having a thickness of 40 Å is grown on top of the lamination, thereby giving a 365-Å thick, p-side multilayered cladding layer composed of multilayered films having a superlattice structure.

(P-Side GaN Contact Layer)

A p-side contact layer of p-type GaN doped with $1 \times 10^{20}/cm^3$ Mg is subsequently grown at 1050° C. to a thickness of 700 Å using trimethyl gallium, ammonia, and biscyclopentadienylmagnesium.

After reaction, the temperature is decreased to room temperature, and then the wafer is annealed at 700° C. in a nitrogen atmosphere in the reaction vessel, so as to reduce the resistivity of the p-type layer.

The wafer is removed from the reaction vessel after annealing. A mask of a predetermined shape is then formed over the surface of the uppermost p-side contact layer, followed by etching the p-side contact layer side of the wafer by reactive ion etching (RIE) such that the surface of the n-side contact layer is exposed.

After etching, a 200-Å thick, translucent p-electrode 10 containing Ni and Au is formed over substantially the entire surface of the uppermost p-side contact layer. On the p-electrode, an Au-containing p-pad electrode for bonding is formed to a thickness of 0.5 Åm. On the exposed surface of the n-side contact layer, an n-electrode containing W and Al is formed. A gallium nitride-based compound semiconductor device is thus produced.

When a forward current of 20 mA is applied across the gallium nitride-based compound semiconductor device, the device exhibits pure green emission at 520 nm.

Trimethyl gallium can be similarly used for gallium nitride-based compound semiconductor devices having different configurations. One such gallium nitride-based compound semiconductor device can be produced as follows. A GaN buffer layer is grown on a substrate using ammonia and trimethyl gallium as source gases. Then, on the first GaN buffer layer are formed a second buffer layer composed of undoped GaN, an n-side contact layer composed of Si-doped GaN, an active layer having a multiple quantum well structure, a single Mg-doped $Al_{0.1}Ga_{0.9}N$ layer, and a p-side contact layer of Mg-doped GaN.

Examples 2-1 to 2-7 given below are encompassed within the first aspect of method 2 of the present invention, and Comparative Example 2-1 is presented for comparison.

Example 2-1

Production of Trimethyl Gallium

A magnetic stirrer bar is placed in a nitrogen-purged, 100-ml glass autoclave. Then, 4.96 g (71 mmol) of gallium and 2.59 g (107 mmol) of magnesium powders having a mean particle diameter of 45 μm (measured by a Mastersizer 2000 manufactured by Malvern Instruments Ltd.) are introduced into the autoclave at room temperature. The mixture is heated until the gallium became completely molten, and then heating the mixture of molten gallium and magnesium powders are continued for 30 more minutes while stirring. The inner temperature of the autoclave during heating is about 60° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the autoclave is decreased to room temperature, 50 ml of diisoamyl ether that has been fully dehydrated with molecular sieves is added to the mixture. Further, 12.08 g (239 mmol) of methyl chloride is introduced slowly into the autoclave, the inner temperature of the autoclave is increased to 90° C., and the mixture is heated for 20 hours while stirring. Although gallium is not dissolved in the diisoamyl ether at the start of reaction, it begins dissolving as the reaction proceeds. At the beginning of the reaction, the gallium content in the diisoamyl ether is 1.42 mol/l, and the magnesium content in the diisoamyl ether is 2.14 mol/l (each content is represented by the number of moles per liter of solvent. This also applies to Examples 2-2 to 2-6 and Comparative Example 2-1).

After the reaction, while evaporating off diisoamyl ether, crude trimethyl gallium is isolated by fractional distillation from the reaction mixture using a glass bead-packed column having a length of 30 cm and a diameter of 1.5 cm.

A quantitative determination of gallium by ICP-AES shows that 5.53 g of crude trimethyl gallium is obtained (yield: 67.7% calculated as the equivalent amount of gallium).

Example 2-2

Production of Trimethyl Gallium

A magnetic stirrer bar is placed in a nitrogen-purged, 100-ml glass autoclave. Then, 5.00 g (72 mmol) of gallium and 2.63 g (108 mmol) of magnesium powders having a mean particle diameter of 45 μm (measured by a Mastersizer 2000 manufactured by Malvern Instruments Ltd.) are introduced into the autoclave at room temperature. The mixture is heated until the gallium becomes completely molten, and then heating the mixture of molten gallium and magnesium powders are continued for 1 more hour while stirring. The inner temperature of the autoclave during heating is about 50° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the autoclave is decreased to room temperature, 50 ml of diisoamyl ether that has been fully dehydrated with molecular sieves is added to the mixture. Further, 12.05 g (239 mmol) of methyl chloride is introduced slowly into the autoclave, the inner temperature of the autoclave is increased to 90° C., and the mixture is heated for 20 hours while stirring. Although gallium is not dissolved in the diisoamyl at the start of reaction, it begins dissolving as the reaction proceeded. At the beginning of the reaction, the gallium content in the diisoamyl ether is 1.44 mol/l, and the magnesium content in the diisoamyl ether is 2.16 mol/l.

After the reaction, while evaporating off diisoamyl ether, crude trimethyl gallium is isolated by fractional distillation from the reaction mixture using a glass bead-packed column having a length of 30 cm and a diameter of 1.5 cm.

A quantitative determination of gallium by ICP-AES shows that 5.77 g of crude trimethyl gallium is obtained (yield: 69.8% calculated as the equivalent amount of gallium).

Example 2-3

Production of Triethyl Gallium

A magnetic stirrer bar is placed in a nitrogen-purged, 100-ml glass autoclave, and then 5.02 g (72 mmol) of gallium and 2.60 g (108 mmol) of magnesium powders having a mean particle diameter of 45 μm (measured by a Mastersizer 2000 manufactured by Malvern Instruments Ltd.) are introduced into the autoclave at room temperature. The mixture is heated until the gallium becomes completely molten, and then heating of the mixture of molten gallium and magnesium powders are continued for 30 more minutes while stirring. The inner temperature of the autoclave during heating is about 60° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the autoclave is decreased to room temperature, 50 ml of diethyl ether that has been fully dehydrated with molecular sieves is added to the mixture. Further, 14.19 g (220 mmol) of ethyl chloride is introduced slowly into the autoclave, the inner temperature of the autoclave is increased to 60° C., and the mixture is heated for 20 hours while stirring. Although gallium is not dissolved in the diethyl ether at the start of reaction, it begins dissolving as the reaction proceeded. At the beginning of the reaction, the gallium content in the diethyl ether is 1.44 mol/l, and the magnesium content in the diisoamyl ether is 2.16 mol/l.

After the reaction, diethyl ether is removed from the reaction mixture by fractional distillation under atmospheric pressure using a glass bead-packed column having a length of 30 cm and a diameter of 1.5 cm, and crude triethyl gallium is then isolated by fractional distillation under a reduced pressure of 100 torr (79 to 81° C.).

A quantitative determination determination of gallium by ICP-AES shows that 7.35 g of crude triethyl gallium is obtained (yield: 65.1% calculated as the equivalent amount of gallium).

Example 2-4

Production of tri-n-propyl Gallium

A magnetic stirrer bar is placed in a nitrogen-purged, 100-ml glass autoclave, and then 5.00 g (72 mmol) of gallium and 2.61 g (109 mmol) of magnesium powders having a mean particle diameter of 45 µm (measured by a Mastersizer 2000 manufactured by Malvern Instruments Ltd.) are introduced into the autoclave at room temperature. The mixture is heated until the gallium becomes completely molten, and then heating the mixture of molten gallium and magnesium powders are continued for 30 more minutes while stirring. The inner temperature of the autoclave during heating is about 60° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the autoclave is decreased to room temperature, 50 ml of diethyl ether that has been fully dehydrated with molecular sieves is added to the mixture. Further, 17.11 g (218 mmol) of n-propyl chloride is introduced slowly into the autoclave, the inner temperature of the autoclave is increased to 60° C., and the mixture is heated for 20 hours while stirring. Although gallium is not dissolved in the diethyl ether at the beginning of the reaction, it begins dissolving as the reaction proceeded. At the beginning of the reaction, the gallium content in the diethyl ether is 1.44 mol/l, and the magnesium content in the diisoamyl ether is 2.18 mol/l.

After the reaction, diethyl ether is separated from the reaction mixture by fractional distillation under atmospheric pressure using a glass bead-packed column having a length of 30 cm and a diameter of 1.5 cm, and crude tri-n-propyl gallium is then isolated by fractional distillation under a reduced pressure of 50 torr (96 to 97° C.).

A quantitative determination of gallium by ICP-AES shows that 9.44 g of crude tri-n-propyl gallium is obtained (yield: 66.0% calculated as the equivalent amount of gallium).

Example 2-5

Production of tri-n-butyl Gallium

A magnetic stirrer bar is placed in a nitrogen-purged, 100-ml glass autoclave, and then 5.05 g (72 mmol) of gallium and 2.65 g (118 mmol) of magnesium powders having a mean particle diameter of 45 µm (measured by a Mastersizer 2000 manufactured by Malvern Instruments Ltd.) are introduced into the autoclave at room temperature. The mixture is heated until the gallium becomes completely molten, and then heating the mixture of molten gallium and magnesium powders are continued for 30 more minutes while stirring. The inner temperature of the autoclave during heating is about 60° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the autoclave is decreased to room temperature, 50 ml of diethyl ether that has been fully dehydrated with molecular sieves is added to the mixture. Further, 21.28 g (230 mmol) of n-butyl chloride is introduced slowly into the autoclave, the inner temperature of the autoclave is increased to 60° C., and the mixture is heated for 20 hours while stirring. Although gallium is not dissolved in the diethyl ether at the beginning of the reaction, it began dissolving as the reaction proceeded. At the beginning of the reaction, the gallium content in the diethyl ether is 1.44 mol/l, and the magnesium content in the diethyl ether is 2.36 mol/l.

After the reaction, diethyl ether is separated from the reaction mixture by fractional distillation under atmospheric pressure using a glass bead-packed column having a length of 30 cm and a diameter of 1.5 cm, and crude tri-n-butyl gallium is then isolated by fractional distillation under a reduced pressure of 5 torr (94 to 95° C.).

A quantitative determination of gallium by ICP-AES shows that 10.94 g of crude tri-n-butyl gallium is obtained (yield: 63.1% calculated as the equivalent amount of gallium).

Example 2-6

Production of Trimethyl Gallium

A magnetic stirrer bar is placed in a nitrogen-purged, 100-ml glass autoclave, and then 5.00 g (72 mmol) of gallium and 2.62 g (109 mmol) of magnesium powders having a mean particle diameter of 45 µm (measured by a Mastersizer 2000 manufactured by Malvern Instruments Ltd.) are introduced into the autoclave at room temperature. The mixture is then heated until the gallium becomes completely molten, and then heating the mixture of molten gallium and magnesium powders are continued for 30 more minutes while stirring. The inner temperature of the autoclave during heating is about 60° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the autoclave is decreased to room temperature, 50 ml of anisole that has been fully dehydrated with molecular sieves is added to the mixture. Further, 11.06 g (217 mmol) of methyl chloride is introduced slowly into the autoclave, the inner temperature of the autoclave is increased to 90° C., and the mixture is heated for 20 hours while stirring. Although gallium is not dissolved in the anisole at the beginning of the reaction, it begins dissolving as the reaction proceeded. At the beginning of the reaction, the gallium content in the anisole is 1.44 mol/l, and the magnesium content in the anisole is 2.18 mol/l.

After the reaction, while evaporating off anisole, crude trimethyl gallium is isolated by fractional distillation from the reaction mixture using a glass bead-packed column having a length of 30 cm and a diameter of 1.5 cm.

A quantitative determination of gallium by ICP-AES shows that 5.42 g of crude trimethyl gallium is obtained (yield: 65.6% calculated as the equivalent amount of gallium).

Comparative Example 2-1

Production without Preactivation by Vacuum Heating

A magnetic stirrer bar is placed in a nitrogen-purged 100-ml glass autoclave. Then, 5.04 g (72 mmol) of gallium and 2.65 g (109 mmol) of magnesium powders having an average particle diameter of 45 µm (measured by a Mastersizer 2000 manufactured by Malvern Instruments Ltd.) are introduced into the autoclave at room temperature.

To the mixture is added 50 ml of diisoamyl ether that has been fully dehydrated with molecular sieves. In addition, 12.03 g (238 mmol) of methyl chloride is introduced slowly into the autoclave. The temperature of the autoclave is increased to 90° C., and the mixture is heated for 20 hours while stirring. Although the gallium is not dissolved in the diisoamyl ether at the beginning of the reaction, it begins dissolving as the reaction proceeded. At the beginning of the reaction, the gallium content in the diisoamyl ether is 1.44 mol/l, and the magnesium content in the diisoamyl ether is 2.18 mol/l.

The gallium has a purity of 6N, and the magnesium has a purity of 3N. The nitrogen has a purity of 6N, a dewpoint of −110° C., and an oxygen content of 1 ppb.

After the reaction, while evaporating off diisoamyl ether, crude trimethyl gallium is isolated from the reaction mixture using a glass bead-packed column having a length of 30 cm and a diameter of 1.5 cm.

A quantitative determination of gallium by ICP-AES shows that 1.41 g of crude trimethyl gallium is obtained (yield: 16.0% calculated as the equivalent amount of gallium).

In connection with the production of trialkyl galliums using alkyl chlorides, the results of the Examples given above show that yields of at least 63%, which are sufficient for practical application, can be achieved by the methods of Examples 2-1 to 2-6 in which, prior to the synthesizing reaction, a mixture of magnesium and molten gallium is heated in a vacuum for preactivation.

In contrast, the yield provided by the method according to Comparative Example 2-1 whose preactivation process involves just stirring magnesium at room temperature is as low as 16.0%. Such a low yield makes the method of Comparative Example 2-1 impractical.

Example 2-7

Production of a Gallium Nitride-Based Compound Semiconductor Device

A gallium nitride-based compound semiconductor device is produced as in Example 1-3 except that trimethyl gallium obtained in Example 2-1 is used in place of trimethyl gallium obtained in Example 1-1.

Examples 3-1 to 3-6 are encompassed within the second aspect of method 2 of the present invention, and Comparative Example 3-1 is presented for comparison.

Example 3-1

Production of Trimethyl Gallium

A magnetic stirrer bar is placed in a nitrogen-purged 300-ml four-necked flask. Then, 10.00 g (143 mmol) of gallium and 5.16 g (215 mmol) of magnesium powders having a mean particle diameter of 45 μm (measured by a Mastersizer 2000 manufactured by Malvern Instruments Ltd.) are introduced into the flask at room temperature. The mixture is heated until the gallium became completely molten, and then heating the mixture of molten gallium and magnesium powders are continued for 30 more minutes while stirring. The inner temperature of the flask during heating is about 60° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the flask is decreased to room temperature, 100 ml of toluene that has been fully dehydrated with molecular sieves is added to the mixture. After the flask is equipped with a dry-ice condenser and the inner temperature of the flask is adjusted to 20° C., 64.4 g (454 mmol) of separately weighed methyl iodide is added dropwise to the solution in the flask while stirring the solution over a period of about 1 hour. All of the methyl iodide is added, and the mixture is stirred for 22 hours while maintaining the inner temperature of the flask at 120° C. Although gallium is not dissolved in the toluene at the start of reaction, it begins dissolving as the reaction proceeded. At the beginning of the reaction, the gallium content in the toluene is 1.43 mol/l, and the magnesium content in the toluene is 2.15 mol/l (each content is represented by the number of moles per liter of solvent. This also applies to Examples 3-2 to 3-5 and Comparative Example 3-1).

After the reaction, a large amount of white magnesium iodide is precipitated. While evaporating off toluene, crude trimethyl gallium is isolated from the reaction mixture using a glass bead-packed column having a length of 30 cm and a diameter of 1.5 cm.

A quantitative determination of gallium by ICP-AES shows that 11.59 g of crude trimethyl gallium is obtained (yield: 70.5% calculated as the equivalent amount of gallium).

Example 3-2

Production of Trimethyl Gallium

A magnetic stirrer bar is placed in a nitrogen-purged, 300-ml four-necked flask. Then, 10.05 g (144 mmol) of gallium and 5.28 g (217 mmol) of magnesium powders having a mean particle diameter of 45 μm (measured by a Mastersizer 2000 manufactured by Malvern Instruments Ltd.) are introduced into the flask at room temperature. The mixture is heated until the gallium became completely molten, and then heating the mixture of molten gallium and magnesium powders are continued for 1 more hour while stirring. The inner temperature of the flask during heating is about 50° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the flask is decreased to room temperature, 100 ml of toluene that has been fully dehydrated with molecular sieves is added to the mixture. After the flask is equipped with a dry-ice condenser and the inner temperature is adjusted to 20° C., 64.5 g (454 mmol) of separately weighed methyl iodide is added dropwise to the solution in the flask while stirring the solution over a period of about 1 hour. All of the methyl iodide is added, and the mixture is stirred for 22 hours while maintaining the inner temperature of the flask at 120° C. Although gallium is not dissolved in the toluene at the beginning of the reaction, it begins dissolving as the reaction proceeded. At the beginning of the reaction, the gallium content in the toluene is 1.44 mol/l, and the magnesium content in the toluene is 2.17 mol/l.

After the reaction, a large amount of white magnesium iodide is precipitated. While evaporating off toluene, crude trimethyl gallium is isolated from the reaction mixture using a glass bead-packed column having a length of 30 cm and a diameter of 1.5 cm.

A quantitative determination of gallium by ICP-AES shows that 11.77 g of crude trimethyl gallium is obtained (yield: 71.2% calculated as the equivalent amount of gallium).

Example 3-3

Production of Triethyl Gallium

A magnetic stirrer bar is placed in a nitrogen-purged, 300-ml four-necked flask. Then, 10.05 g (144 mmol) of gallium and 5.18 g (216 mmol) of magnesium powders having a mean particle diameter of 45 μm (measured by a Mastersizer 2000 manufactured by Malvern Instruments Ltd.) are introduced into the flask at room temperature. The mixture is heated until the gallium became completely molten, and then heating the mixture of molten gallium and magnesium powders are continued for 30 more minutes while stirring. The inner temperature of the flask during heating is about 60° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the flask is decreased to room temperature, 100 ml of hexane that has been fully dehydrated with molecular sieves is added to the mixture. After the flask is equipped with a dry-ice condenser and the inner temperature is adjusted to 20° C., 67.08 g (430 mmol) of separately weighed ethyl iodide is added dropwise to the solution in the flask while stirring the solution over a period of about 1 hour. All of the ethyl iodide is added, and the mixture is heated while stirring in order for the hexane to lightly reflux. Although gallium is solid at the beginning of the reaction, it begins dissolving in the hexane as the reaction proceeded. At the beginning of the reaction, the gallium content in the hexane is 1.44 mol/l, and the magnesium content in the hexane is 2.16 mol/l.

After the reaction, a large amount of white magnesium iodide is precipitated. The hexane is removed from the reaction mixture by fractional distillation under atmospheric pressure using a glass bead-packed column having a length of 30 cm and a diameter of 1.5 cm, and crude triethyl gallium is then isolated by fractional distillation under a reduced pressure of 100 torr (79 to 81° C.).

A determination of gallium by ICP-AES shows that 15.50 g of crude triethyl gallium is obtained (yield: 68.7% calculated as the equivalent amount of gallium).

Example 3-4

Production of tri-n-propyl Gallium

A magnetic stirrer bar is placed in a nitrogen-purged, 300-ml four-necked flask. Then, 10.02 g (144 mmol) of gallium and 5.30 g (221 mmol) of magnesium powders having a mean particle diameter of 45 μm (measured by a Mastersizer 2000 manufactured by Malvern Instruments Ltd.) are introduced into the flask at room temperature. The mixture is heated until the gallium becomes completely molten, and then heating the mixture of molten gallium and magnesium powders are continued for 30 more minutes while stirring. The inner temperature of the flask during heating is about 60° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the flask is decreased to room temperature, 100 ml of hexane that has been fully dehydrated with molecular sieves is added to the mixture. After the flask is equipped with a dry-ice condenser and the inner temperature is adjusted to 20° C., 74.8 g (440 mmol) of separately weighed n-propyl iodide is added dropwise to the solution in the flask while stirring the solution over a period of about 1 hour. All of the n-propyl iodide is added, and the mixture is stirred for 22 hours while maintaining the inner temperature of the flask at 120° C. Although gallium is not dissolved in the hexane at the beginning of the reaction, it begins dissolving as the reaction proceeded. At the beginning of the reaction, the gallium content in the hexane is 1.44 mol/l, and the magnesium content in the hexane is 2.21 mol/l.

After the reaction, a large amount of white magnesium iodide is precipitated. The hexane is removed from the reaction mixture by fractional distillation under atmospheric pressure using a glass bead-packed column having a length of 30 cm and a diameter of 1.5 cm, and crude tri-n-propyl gallium is then isolated by fractional distillation under a reduced pressure of 50 torr (97 to 98° C.).

A quantitative determination of gallium by ICP-AES shows that 19.77 g of crude tri-n-propyl gallium is obtained (yield: 69.1% calculated as the equivalent amount of gallium).

Example 3-5

Production of tri-n-butyl Gallium

A magnetic stirrer bar is placed in a nitrogen-purged, 300-ml four-necked flask. Then, 10.00 g (143 mmol) of gallium and 5.16 g (215 mmol) of magnesium powders having a mean particle diameter of 45 μm (measured by a Mastersizer 2000 manufactured by Malvern Instruments Ltd.) are introduced into the flask at room temperature. The mixture is heated until the gallium became completely molten, and then heating the mixture of molten gallium and magnesium powders are continued for 30 more minutes while stirring. The inner temperature of the flask during heating is about 60° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the flask is decreased to room temperature, 100 ml of hexane that has been fully dehydrated with molecular sieves is added to the mixture. After the flask is equipped with a dry-ice condenser and the inner temperature is adjusted to 20° C., 79.12 g of separately weighed n-butyl iodide (430 mmol) is added dropwise to the solution in the flask while stirring the solution over a period of about 1 hour. All of the n-butyl iodide is added, and the mixture is stirred for 22 hours while maintaining the inner temperature of the flask at 120° C. Although gallium is not dissolved in the hexane at the beginning of the reaction, it begins dissolving as the reaction proceeded. At the beginning of the reaction, the gallium content in the hexane is 1.43 mol/l, and the magnesium content in the hexane is 2.15 mol/l.

After the reaction, a large amount of white magnesium iodide is precipitated. The hexane is removed from the reaction mixture by fractional distillation under atmospheric pressure using a glass bead-packed column having a length of 30 cm and a diameter of 1.5 cm, and crude tri-n-butyl gallium is then isolated by fractional distillation under a reduced pressure of 50 torr (97 to 98° C.).

A quantitative determination of gallium by ICP-AES shows that 22.96 g of crude tri-n-butyl gallium is obtained (yield: 66.7% calculated as the equivalent amount of gallium).

Comparative Example 3-1

Production without Preactivation by Vacuum Heating

A magnetic stirrer bar is placed in a nitrogen-purged 300-ml four-necked flask. Then, 10.01 g (144 mmol) of gallium and 5.23 g (216 mmol) of magnesium powders having an average particle diameter of 45 μm (measured by a Mastersizer 2000 manufactured by Malvern Instruments Ltd.) are introduced into the autoclave at room temperature.

To the mixture is added 100 ml of toluene that has been fully dehydrated with molecular sieves. After the flask is equipped with a dry-ice condenser and the inner temperature of the flask is adjusted to 20° C., 64.0 g (451 mmol) of separately weighed methyl iodide is added dropwise to the solution in the flask while stirring the solution over a period of about 1 hour. All of the methyl iodide is added, and the mixture is stirred for 22 hours while maintaining the inner temperature of the flask at 120° C. Although gallium is not dissolved in the toluene at the beginning of the reaction, it begins dissolving as the reaction proceeded. At the beginning of the reaction, the gallium content in the toluene is 1.44 mol/l, and the magnesium content in the toluene is 2.16 mol/l.

The gallium has a purity of 6N, and the magnesium has a purity of 3N. The nitrogen has a purity of 6N, a dewpoint of −110° C., and an oxygen content of 1 ppb.

After the reaction, a large amount of white magnesium iodide is precipitated while evaporating off toluene, crude trimethyl gallium is isolated from the reaction mixture by fractional distillation using a glass bead-packed column having a length of 30 cm and a diameter of 1.5 cm.

A quantitative determination of gallium by ICP-AES shows that 2.91 g of crude trimethyl gallium is obtained (yield: 17.6% calculated as the equivalent amount of gallium).

In connection with the production of trialkyl galliums using hydrocarbons, the results of the Examples given above show that yields of at least 66%, which are sufficient for practical application, can be achieved by the methods of Examples 3-1 to 3-5 in which, prior to the reaction, a mixture of molten gallium and magnesium is heated in a vacuum for preactivation.

In contrast, the yield provided by the method according to Comparative Example 3-1 whose preactivation process involves just stirring magnesium at room temperature is as low as 17.6%. Such a low yield makes the method of Comparative Example 3-1 impractical.

Example 3-6

Production of a Gallium Nitride-Based Compound Semiconductor Device

A gallium nitride-based compound semiconductor device is produced as in Example 1-3 except that trimethyl gallium obtained in Example 3-1 is used in place of trimethyl gallium obtained in Example 1-1.

Examples 4-1 to 4-4 are encompassed within the third aspect of method 2 of the present invention, and Comparative Example 4-1 is presented for comparison.

Example 4-1

Production of Trimethyl Gallium

A magnetic stirrer bar is placed in a nitrogen-purged 100-ml glass autoclave. Then, 4.97 g (71 mmol) of gallium and 2.71 g (112 mmol) of magnesium powders having a mean particle diameter of 45 μm (measured by a Mastersizer 2000 manufactured by Malvern Instruments Ltd.) are introduced into the autoclave at room temperature. The mixture is heated until the gallium became completely molten, and then heating the mixture of molten gallium and magnesium powders are continued for 30 more minutes while stirring. The inner temperature of the autoclave during heating is about 60° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the autoclave is decreased to room temperature, 50 ml of toluene that has been fully dehydrated with molecular sieves is added to the mixture. Further, 12.97 g (257 mmol) of methyl chloride is introduced slowly into the autoclave, the inner temperature of the autoclave is increased to 90° C., and the mixture is heated for 20 hours while stirring. Although gallium is not dissolved in the toluene at beginning of the reaction, it begins dissolving in it as the reaction proceeded. At the beginning of the reaction, the gallium content in the toluene is 1.42 mol/l, and the magnesium content in the toluene is 2.24 mol/l (each content is represented by the number of moles per liter of solvent. This also applies to Examples 4-2 to 4-4).

After the reaction, while evaporating off toluene, crude trimethyl gallium is isolated by fractional distillation from the reaction mixture using a glass bead-packed column having a length of 30 cm and a diameter of 1.5 cm.

A determination of gallium by ICP-AES shows that 1.99 g of crude trimethyl gallium is obtained (yield: 24.4% calculated as the equivalent amount of gallium).

Example 4-2

Production of Trimethyl Gallium

A magnetic stirrer bar is placed in a nitrogen-purged, 100-ml glass autoclave. Then, 5.05 g (72 mmol) of gallium and 2.70 g (111 mmol) of magnesium powders having a mean particle diameter of 45 μm (measured by a Mastersizer 2000 manufactured by Malvern Instruments Ltd.) are introduced into the autoclave at room temperature. The mixture is heated until the gallium becomes completely molten, and then heating the mixture of molten gallium and magnesium powders are continued for 1 more hour while stirring. The inner temperature of the autoclave during heating is about 50° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the autoclave is decreased to room temperature, 50 ml of toluene that had been fully dehydrated with molecular sieves is added to the mixture. Further, 12.90 g (255 mmol) of methyl chloride is introduced slowly into the autoclave, the inner temperature of the autoclave is increased to 90° C., and the mixture is heated for 20 hours while stirring. Although gallium is not dissolved in the toluene at the beginning of the reaction, it begins dissolving as the reaction proceeded. At the beginning of the reaction, the gallium content in the toluene is 1.44 mol/l, and the magnesium content in the toluene is 2.22 mol/l.

After the reaction, while evaporating off toluene, crude trimethyl gallium is isolated by fractional distillation from the reaction mixture using a glass bead-packed column having a length of 30 cm and a diameter of 1.5 cm.

A determination of gallium by ICP-AES shows that 1.99 g of crude trimethyl gallium is obtained (yield: 24.1% calculated as the equivalent amount of gallium).

Example 4-3

Production of Triethyl Gallium

A magnetic stirrer bar is placed in a nitrogen-purged, 100-ml glass autoclave. Then, 5.00 g (72 mmol) of gallium and 2.62 g (109 mmol) of magnesium powders having a mean particle diameter of 45 μm (measured by a Mastersizer 2000 manufactured by Malvern Instruments Ltd.) are introduced into the autoclave at room temperature. The mixture is heated until the gallium become completely molten, and then heating the mixture of molten gallium and magnesium powders are continued for 30 more minutes while stirring. The inner temperature of the autoclave during heating is about 60° C. The mixture is then subjected to preactivation by heating while stirring at 90° C. for 3 hours at a degree of vacuum of 10 Pa.

The gallium has a purity of 6N, and the magnesium has a purity of 3N. The nitrogen has a purity of 6N, a dewpoint of −110° C., and an oxygen content of 1 ppb.

After the inner temperature of the autoclave is decreased to room temperature, 50 ml of hexane that has been fully dehydrated with molecular sieves is added to the mixture. Further, 13.99 g of (217 mmol) ethyl chloride is introduced slowly into the autoclave, the inner temperature of the autoclave is increased to 90° C., and the mixture is heated for 20 hours while stirring. Although gallium is not dissolved in the hexane at the beginning of the reaction, it begins dissolving in it as the reaction proceeded. At the beginning of the reaction, the gallium content in the hexane is 1.44 mol/l, and the magnesium content in the hexane is 2.18 mol/l.

After the reaction, the hexane is removed from the reaction mixture by fractional distillation under atmospheric pressure using a glass bead-packed column having a length of 30 cm and a diameter of 1.5 cm, and crude triethyl gallium is then isolated by fractional distillation under a reduced pressure of 100 torr (79 to 81° C.).

A quantitative determination of gallium by ICP-AES shows that 2.10 g of crude triethyl gallium is obtained (yield: 18.6% calculated as the equivalent amount of gallium).

Comparative Example 4-1

Production without Preactivation by Vacuum Heating

A magnetic stirrer bar is placed in a nitrogen-purged 100-ml glass autoclave. Then, 4.99 g (72 mmol) of gallium and 2.68 g (110 mmol) of magnesium powders having an average particle diameter of 45 μm (measured by a Mastersizer 2000 manufactured by Malvern Instruments Ltd.) are introduced into the autoclave at room temperature. The gallium has a purity of 6N, and the magnesium has a purity of 3N. The nitrogen has a purity of 6N, a dewpoint of −110° C., and an oxygen content of 1 ppb.

To the mixture is added 50 ml of toluene that has been fully dehydrated with molecular sieves. In addition, 12.82 g (254 mmol) of methyl chloride is introduced slowly into the autoclave. The temperature of the autoclave is increased to 90° C., and the mixture is heated for 20 hours while stirring. Although the gallium is not dissolved in the toluene at the beginning of the reaction, it begins dissolving as the reaction proceeded. At the beginning of the reaction, the gallium content in the toluene is 1.44 mol/l, and the magnesium content in the toluene is 2.20 mol/l.

After the reaction, while evaporating off toluene, crude trimethyl gallium is isolated from the reaction mixture using a glass bead-packed column having a length of 30 cm and a diameter of 1.5 cm.

A quantitative determination of gallium by ICP-AES shows that 0.091 g of crude trimethyl gallium is obtained (yield: 1.1% calculated as the equivalent amount of gallium).

In connection with the production of trialkyl galliums using alkyl chlorides in hydrocarbon solvents, the results of the examples presented above show that yields of at least 18% can be achieved by the methods of Examples 4-1 to 4-3 in which, prior to the reaction, a mixture of molten gallium and magnesium is heated in a vacuum for preactivation.

In contrast, the yield provided by the method according to Comparative Example 4-1 whose preactivation process involves just stirring magnesium at room temperature is as low as 1.1%. That is, a trialkyl gallium is barely obtainable.

Example 4-4

Production of a Gallium Nitride-Based Compound Semiconductor Device

A gallium nitride-based compound semiconductor device is produced as in Example 1-3 except that trimethyl gallium obtained in Example 4-1 is used in place of trimethyl gallium obtained in Example 1-1.

Examples 5-1 to 5-7 are encompassed within method 3 of the present invention.

Example 5-1

Production of Trimethyl Gallium (1) Production of $Ga_2Me_3I_3$

A magnetic stirrer bar is placed in a nitrogen-purged, 100-ml glass autoclave, and then 5.00 g (72 mmol) of gallium having a purity of 6N and 22.78 g (161 mmol) of methyl iodide are introduced into the autoclave at room temperature. The temperature inside the autoclave is increased to 90° C., and the mixture is heated while stirring at 90° C. for 24 hours.

All the gallium dissolves into a yellow liquid. The resulting product is identified by its IR spectrum and Raman spectrum, with reference to the description of M. J. S. Gynane, I. J. Worral, *J. Organomet. Chem.*, 40, C59 (1972).

(2) Production of Methyl Magnesium Iodide

Into a nitrogen-purged, 300-ml four-neck flask are introduced at room temperature 4.01 g (167 mmol) of magnesium shavings having a purity of 3 N and 68 ml of diisoamyl ether which had been fully dehydrated using molecular sieves. After the flask is equipped with a dry-ice condenser and the inner temperature is adjusted to 20° C., 27.89 g (197 mmol) of methyl iodide is added dropwise to the solution in the flask over about 2 hours. During this procedure, the temperature in the flask is controlled so as not to exceed 40° C. Following the dropwise addition, stirring is carried out at room temperature for 12 hours.

The resulting reaction mixture is filtered. Methyl magnesium iodide is generated in a yield of 97.0% (162 mmol), as measured according to the Gilman double titration method (described in H. Gilman, F. K. Cantledge, *J. Organomet. Chem.*, 2, 447 (1964)).

(3) Reaction of $Ga_2Me_3I_3$ and Methyl Magnesium Iodide

The entire quantity of $Ga_2Me_3I_3$ produced above and 48 ml of diisoamyl ether which has been fully dehydrated using molecular sieves are introduced at room temperature into a nitrogen-purged, 300-ml four-neck flask. After the flask is equipped with a dry-ice condenser and the inner temperature is adjusted to 20° C., a diisoamyl ether solution of 56 g (114 mmol) of the methyl magnesium iodide prepared above is slowly added dropwise. Following the dropwise addition, the temperature inside the autoclave is raised to 90° C., and heating and stirring are then carried out for 6 hours.

The nitrogen used in the productions of $Ga_2Me_3I_3$, methyl magnesium iodide and trimethyl gallium has a purity of 6N, a dew point of −110° C., and an oxygen content of 1 ppb. Right after the introduction of methyl magnesium iodide, the $Ga_2Me_3I_3$ content in the solvent is 0.31 mol/l and the methyl magnesium iodide content in the solvent is 0.97 mol/l (each content is represented by the number of moles per liter of solvent. This also applies to Examples 5-2 to 5-7).

After the reaction, while evaporating off diisoamyl ether, crude trimethyl gallium is isolated by fractional distillation from the reaction mixture using a glass bead-packed column having a length of 30 cm and a diameter of 1.5 cm.

A quantitative determination of gallium by ICP-AES shows that 6.09 g of crude trimethyl gallium is obtained (yield: 73.5% calculated as the equivalent amount of gallium).

Example 5-2

Production of Trimethyl Gallium (1) Reaction of $Ga_2Me_3I_3$ and Trimethyl Aluminum A magnetic stirrer bar is placed in a nitrogen-purged, 100-ml glass autoclave, and then $Ga_2Me_3I_3$ produced in the same manner and amount as in Example 5-1 and 50 ml of toluene which has been fully dehydrated using molecular sieves are introduced at room temperature. Next, 8.36 g (116 mmol) of commercially available trimethyl aluminum is introduced, and heating and stirring are then performed at 120° C. for 20 hours.

The nitrogen used herein has a purity of 6N, a dew point of −110° C., and an oxygen content of 1 ppb. At the point when the addition of trimethyl aluminum is completed, the solvent has a $Ga_2Me_3I_3$ content of 0.50 mol/l and a trimethyl aluminum content of 1.61 mol/l.

After the reaction, while evaporating off toluene, crude trimethyl gallium is isolated by fractional distillation from the reaction mixture using a glass bead-packed column having a length of 30 cm and a diameter of 1.5 cm.

A quantitative determination of gallium by ICP-AES shows that 6.74 g of crude trimethyl gallium is obtained (yield: 81.5% calculated as the equivalent amount of gallium).

Example 5-3

Production of Trimethyl Gallium (1) Production of $Ga_2Me_3Br_3$

A magnetic stirrer bar is placed in a nitrogen-purged, 100-ml glass autoclave, and then 5.00 g (72 mmol) of gallium having a purity of 6N and 14.73 g (155 mmol) of methyl bromide are introduced into the autoclave at room temperature. The temperature inside the autoclave is increased to 90° C., and the mixture is heated while stirring at 90° C. for 24 hours. All the gallium dissolved into a yellow liquid.

The resulting product is identified by its IR spectrum and Raman spectrum, with reference to the description of M. J. S. Gynane, I. J. Worral, *J. Organomet. Chem.*, 40, C59 (1972).

(2) Reaction of $Ga_2Me_3Br_3$ and Methyl Magnesium Iodide

The entire quantity of $Ga_2Me_3Br_3$ produced above and 48 ml of diisoamyl ether which has been fully dehydrated using molecular sieves are introduced at room temperature into a nitrogen-purged, 300-ml four-neck flask. After the flask is equipped with a dry-ice condenser and the inner temperature is adjusted to 20° C., a diisoamyl ether solution of 56 g (114 mmol) of the methyl magnesium iodide produced in Example 5-1 is slowly added dropwise. Following the dropwise addition, the temperature inside the autoclave is raised to 90° C., and heating and stirring are then carried out for 6 hours.

The nitrogen used in the productions of $Ga_2Me_3Br_3$, methyl magnesium iodide and trimethyl gallium has a purity of 6N, a dew point of −110° C., and an oxygen content of 1 ppb. Right after the introduction of methyl magnesium iodide, the $Ga_2Me_3Br_3$ content in the solvent is 0.32 mol/l and the methyl magnesium iodide content in the solvent is 1.02 mol/l.

After the reaction, while evaporating off diisoamyl ether, crude trimethyl gallium is isolated by fractional distillation from the reaction mixture using a glass bead-packed column having a length of 30 cm and a diameter of 1.5 cm.

A quantitative determination of gallium by ICP-AES shows that 5.92 g of crude trimethyl gallium is obtained (yield: 71.5% calculated as the equivalent amount of gallium).

Example 5-4

Production of Triethyl Gallium (1) Production of $Ga_2Et_3I_3$

A magnetic stirrer bar is placed in a nitrogen-purged, 100-ml glass autoclave, and then 5.00 g (72 mmol) of gallium having a purity of 6N and 24.11 g (155 mmol) of ethyl iodide are introduced into the autoclave at room temperature. The temperature inside the autoclave is increased to 90° C., and the mixture is heated while stirring at 90° C. for 24 hours. All the gallium dissolves into a yellow liquid. The resulting product is identified by its IR spectrum and Raman spectrum, with reference to the description of M. J. S. Gynane, I. J. Worral, *J. Organomet. Chem.*, 40, C59 (1972).

(2) Production of Ethyl Magnesium Iodide

Into a nitrogen-purged, 300-ml four-neck flask are introduced at room temperature 4.17 g (174 mmol) of magnesium shavings having a purity of 3 N and 68 ml of diethyl ether which has been fully dehydrated using molecular sieves. After the flask is equipped with a dry-ice condenser and the inner temperature is adjusted to 20° C., 29.65 g (190 mmol) of ethyl iodide is added dropwise to the solution in the flask over about 2 hours. During this procedure, the temperature in the flask is controlled such that the diethyl ether is at a light boil. Following the dropwise addition, stirring is carried out at room temperature for 12 hours.

The resulting reaction mixture is filtered. Ethyl magnesium iodide is generated in a yield of 98.0% (171 mmol), as measured according to the Gilman double titration method (described in H. Gilman, F. K. Cantledge, *J. Organomet. Chem.*, 2, 447 (1964)).

(3) Reaction of $Ga_2Et_3I_3$ and Ethyl Magnesium Iodide

The entire quantity of $Ga_2Et_3I_3$ produced above and 48 ml of diethyl ether which has been fully dehydrated using molecular sieves are introduced at room temperature into a nitrogen-purged, 300-ml four-neck flask. After the flask is equipped with a dry-ice condenser and the inner temperature is adjusted to 20° C., a diethyl ether solution of 56 g (114 mmol) of the ethyl magnesium iodide produced above is slowly added dropwise. Following the dropwise addition, the mixture is heated and refluxed for 6 hours.

The nitrogen used in the productions of $Ga_2Et_3I_3$, ethyl magnesium iodide and triethyl gallium has a purity of 6N, a dew point of −110° C., and an oxygen content of 1 ppb. Right after the introduction of ethyl magnesium iodide, the $Ga_2Et_3I_3$ content in the solvent is 0.30 mol/l and the ethyl magnesium iodide content in the solvent is 0.96 mol/l.

After the reaction, diethyl ether is removed from the reaction mixture by fractional distillation under atmospheric pressure using a glass bead-packed column having a length of 30 cm and a diameter of 1.5 cm, and crude triethyl gallium is then isolated by fractional distillation under a reduced pressure of 100 torr (79 to 81° C.).

A quantitative determination of gallium by ICP-AES shows that 7.90 g of crude triethyl gallium is obtained (yield: 69.9% calculated as the equivalent amount of gallium).

Example 5-5

Production of Trimethyl Gallium

Reaction of $Ga_2Et_3I_3$ and ethyl lithium $Ga_2Et_3I_3$ produced in the same manner and amount as in Example 5-4 and 48 ml of diethyl ether which has been fully dehydrated using molecular sieves are introduced at room temperature into a nitrogen-purged, 300-ml four-neck flask. After the flask is equipped with a dry-ice condenser and the inner temperature is adjusted to 20° C., 72 ml of a diethyl ether solution of commercial available ethyl lithium (72 mmol, ethyl lithium concentration of 1.0 mol/l) is slowly added dropwise. Following the dropwise addition, the mixture is heated and refluxed for 6 hours.

The nitrogen used herein has a purity of 6N, a dew point of −110° C., and an oxygen content of 1 ppb. Right after the introduction of ethyl lithium, the $Ga_2Et_3I_3$ content in the solvent is 0.27 mol/l and the ethyl lithium content in the solvent is 0.54 mol/l.

After the reaction, diethyl ether is removed from the reaction mixture by fractional distillation under atmospheric pressure using a glass bead-packed column having a length of 30 cm and a diameter of 1.5 cm, and crude triethyl gallium is then isolated by fractional distillation under a reduced pressure of 100 torr (79 to 81° C.).

A quantitative determination of gallium by ICP-AES shows that 9.20 g of crude triethyl gallium is obtained (yield: 81.5% calculated as the equivalent amount of gallium).

Example 5-6

Production of Trimethyl Gallium

Reaction of $Ga_2Me_3I_3$ and Dimethyl Zinc

A magnetic stirrer bar is placed in a nitrogen-purged, 100-ml glass autoclave, and then $Ga_2Me_3I_3$ produced in the same manner and amount as in Example 5-1 and 50 ml of toluene which has been fully dehydrated using molecular sieves are introduced at room temperature. Next, 5.73 g (60 mmol) of commercially available dimethyl zinc is introduced, and heating and stirring are then performed at 120° C. for 20 hours.

The nitrogen used herein has a purity of 6N, a dew point of −110° C., and an oxygen content of 1 ppb. Right after the introduction of dimethyl zinc, the solvent has a $Ga_2Me_3I_3$ content of 0.50 mol/l and a dimethyl zinc content of 0.87 mol/l.

After the reaction, while evaporating off toluene, crude trimethyl gallium is isolated by fractional distillation from the reaction mixture using a glass bead-packed column having a length of 30 cm and a diameter of 1.5 cm.

A quantitative determination of gallium by ICP-AES shows that 7.08 g of crude trimethyl gallium is obtained (yield: 85.7% calculated as the equivalent amount of gallium).

The Examples presented above show that a trialkyl gallium can be obtained in a yield of about at least 70%, which is sufficient for practical use, by alkylating an alkylgallium halide with an alkyl metal.

Example 5-7

Production of a Gallium Nitride-Based Compound Semiconductor Device

A gallium nitride-based compound semiconductor device is produced as in Example 1-3 except that trimethyl gallium obtained in Example 5-1 is used in place of trimethyl gallium obtained in Example 1-1.

We claim:

1. A method for producing a trialkyl gallium comprising the steps of:
    reacting gallium, magnesium, and at least one alkyl halide in at least one ether to produce a trialkyl gallium; and
    diluting during the reaction the reaction system with at least one ether,
    wherein the trialkyl gallium is produced without using a gallium-magnesium alloy;
    wherein the reaction system has a magnesium content of 5 mol/l or greater at the beginning of the reaction, and the reaction system is diluted to have a total magnesium content of 4 mol/l or less; and
    wherein the magnesium is in the form of ribbons, shavings, chips or grains.

2. The method according to claim 1, wherein gallium, magnesium, and at least one alkyl halide are reacted by introducing at least one alkyl halide into a mixture of gallium, magnesium, and at least one ether.

3. The method according to claim 2, wherein at least one alkyl halide is introduced dropwise into the mixture of gallium, magnesium, and at least one ether.

4. The method according to claim 1, wherein the reaction system is diluted within about 30 minutes of when an alkyl magnesium halide and magnesium halide precipitate from the reaction system and the temperature increase of the reaction system has ceased (Ts).

5. The method according to claim 1, wherein 1 to 10 mol of magnesium is used per mol of gallium.

6. The method according to claim 1, wherein the at least one alkyl halide is at least one member selected from the group consisting of alkyl iodides and alkyl bromides.

7. The method according to claim 1, wherein the at least one alkyl halide contains a $C_{1-10}$ alkyl group.

8. A method for producing a trialkyl gallium comprising the steps of:
    heating in a vacuum a mixture of magnesium and molten gallium, and reacting the vacuum-heated mixture with at least one alkyl halide in at least one solvent to produce a trialkyl gallium, wherein the at least one solvent is an ether and the at least one alkyl halide is an alkyl chloride.

9. The method according to claim 8, wherein the vacuum heating is performed at 1000 Pa or less and at 60° C. or higher.

10. The method according to claim 8, further comprising the step of maintaining the magnesium and molten gallium in a mixed state, the step being performed prior to the step of vacuum heating.

11. The method according to claim 10, wherein the step of maintaining the magnesium and molten gallium in a mixed state is performed at 40 to 60° C.

12. The method according to claim 8, wherein 1 to 10 mol of magnesium is used per mol of gallium.

13. The method according to claim 8, wherein the at least one alkyl chloride contains a $C_{1-10}$ alkyl group.

14. A method for producing a trialkyl gallium comprising the steps of:

heating in a vacuum a mixture of magnesium and molten gallium, and reacting the vacuum-heated mixture with at least one alkyl halide in at least one solvent to produce a trialkyl gallium, wherein the at least one solvent is a hydrocarbon, and the at least one alkyl halide is selected from the group consisting of alkyl chlorides and alkyl bromides.

15. The method according to claim 14, wherein the vacuum heating is performed at 1000 Pa or less and at 60° C. or higher.

16. The method according to claim 14, further comprising the step of maintaining the magnesium and molten gallium in a mixed state, the step being performed prior to the step of vacuum heating.

17. The method according to claim 16, wherein the step of maintaining the magnesium and molten gallium in a mixed state is performed at 40 to 60° C.

18. The method according to claim 14, wherein 1 to 20 mol of magnesium is used per mol of gallium.

19. The method according to claim 14, wherein the at least one alkyl halide contains a $C_{1-10}$ alkyl group.

* * * * *